(12) United States Patent
Haubert

(10) Patent No.: US 12,076,505 B2
(45) Date of Patent: Sep. 3, 2024

(54) MAGNETIC CONNECTOR FOR STEERABLE MEDICAL DEVICE

(71) Applicant: Canon U.S.A., Inc., Melville, NY (US)

(72) Inventor: Zachary Hamilton Haubert, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 836 days.

(21) Appl. No.: 17/133,184

(22) Filed: Dec. 23, 2020

(65) Prior Publication Data

US 2022/0040450 A1 Feb. 10, 2022

Related U.S. Application Data

(60) Provisional application No. 63/062,211, filed on Aug. 6, 2020, provisional application No. 63/062,313, filed on Aug. 6, 2020.

(51) Int. Cl.
*A61M 25/01* (2006.01)
*A61B 1/00* (2006.01)
*A61B 1/005* (2006.01)
*A61B 5/00* (2006.01)
*A61M 25/00* (2006.01)

(52) U.S. Cl.
CPC ..... *A61M 25/0127* (2013.01); *A61B 1/00121* (2013.01); *A61B 1/00149* (2013.01); *A61B 1/0057* (2013.01); *A61B 5/0066* (2013.01); *A61B 5/0075* (2013.01); *A61B 5/0084* (2013.01); *A61M 25/0097* (2013.01); *A61M 25/0147* (2013.01); *A61M 2025/0166* (2013.01);

(Continued)

(58) Field of Classification Search
CPC .......... A61M 25/0127; A61M 25/0097; A61B 1/00121; A61B 1/00149; A61B 1/0057; A61B 5/0066; A61B 5/0075; A61B 5/0084
USPC ....................................................... 604/528
See application file for complete search history.

(56) References Cited

U.S. PATENT DOCUMENTS 5,954,446 A 9/1999 Ireland
6,858,005 B2 2/2005 Ohline et al.
(Continued)

FOREIGN PATENT DOCUMENTS

JP 2007-29274 A 2/2007
JP 2019-511260 A 4/2019
(Continued)

*Primary Examiner* — Phillip A Gray
(74) *Attorney, Agent, or Firm* — Canon U.S.A., Inc., IP Division

(57) ABSTRACT

In a robot-assisted steerable medical device, such as a catheter, a magnetic connector hub is configured to establish mechanical and magnetic connection between a drive cable and an actuator, or between multiple modules in a single insert-and-twist motion. The connector hub creates a magnetic breakaway feature for automatically decoupling the actuator from the drive cable, while the catheter remains attached. This prevents damage to the catheter/tool and/or patient when an excessive force is applied, and adds a safety element and helps protect the patient. And when the breakaway occurs the system can be automatically reengaged catheter without damage, so that normal operation can resume. Connection can also be broken at any point in the operation based on threshold forces or emergency situations.

23 Claims, 14 Drawing Sheets

(52) U.S. Cl.
CPC ............ *A61M 2205/332* (2013.01); *A61M 2205/3327* (2013.01)

(56) References Cited

U.S. PATENT DOCUMENTS

| | | |
|---|---|---|
| 8,251,084 B2 | 8/2012 | Brown |
| 8,337,783 B2 | 12/2012 | Locascio et al. |
| 9,114,540 B2 | 8/2015 | Claffee et al. |
| 9,604,838 B2 | 3/2017 | Cornett et al. |
| 9,629,522 B2 | 4/2017 | Ando |
| 9,629,688 B2 | 4/2017 | Robert et al. |
| 10,105,036 B2 | 10/2018 | Julian et al. |
| 10,292,760 B2 | 5/2019 | Haughton et al. |
| 10,722,296 B2 | 7/2020 | Haughton et al. |
| 2006/0287576 A1 | 12/2006 | Tsuji et al. |
| 2007/0232856 A1* | 10/2007 | Ueno ............ A61B 1/009 600/145 |
| 2008/0287738 A1* | 11/2008 | Adachi ............ A61B 1/0016 600/118 |
| 2011/0018663 A1 | 1/2011 | Fullerton et al. |
| 2011/0266904 A1 | 11/2011 | Stefanini et al. |
| 2013/0090529 A1 | 4/2013 | Boulais |
| 2015/0112143 A1 | 4/2015 | Ando |
| 2017/0325817 A1 | 11/2017 | Racenet et al. |
| 2020/0107898 A1 | 4/2020 | Kim et al. |

FOREIGN PATENT DOCUMENTS

| | | |
|---|---|---|
| JP | 2020-099300 A | 7/2020 |
| WO | 2006/059722 A1 | 6/2006 |

\* cited by examiner

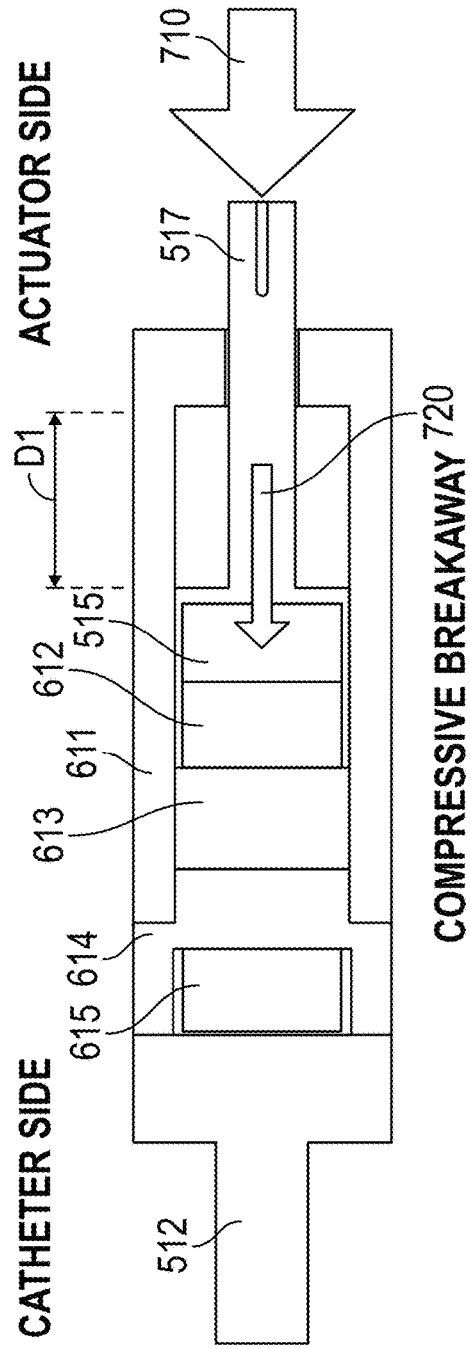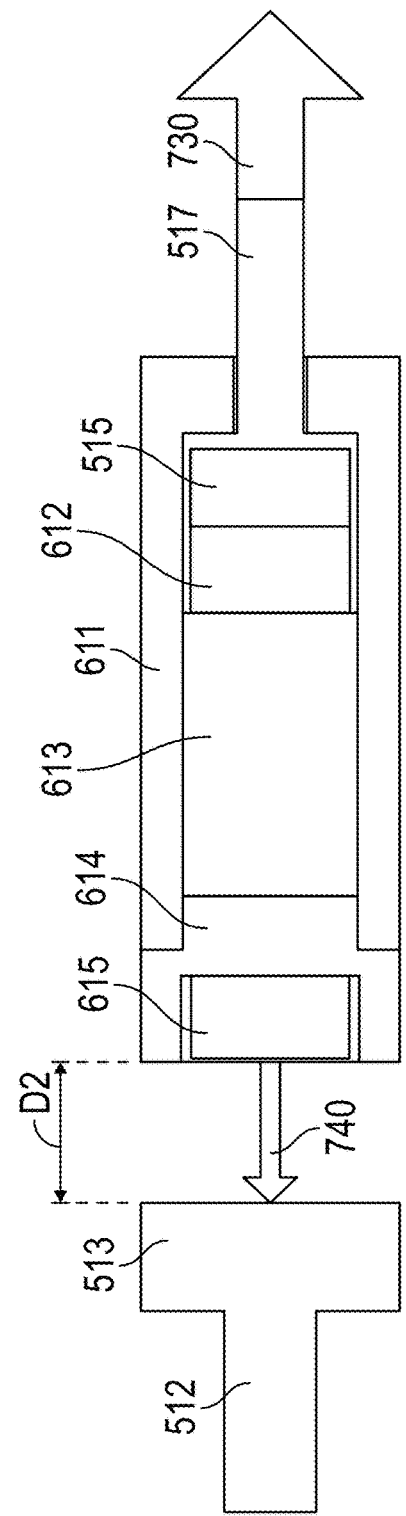

ACTUATOR SIDE

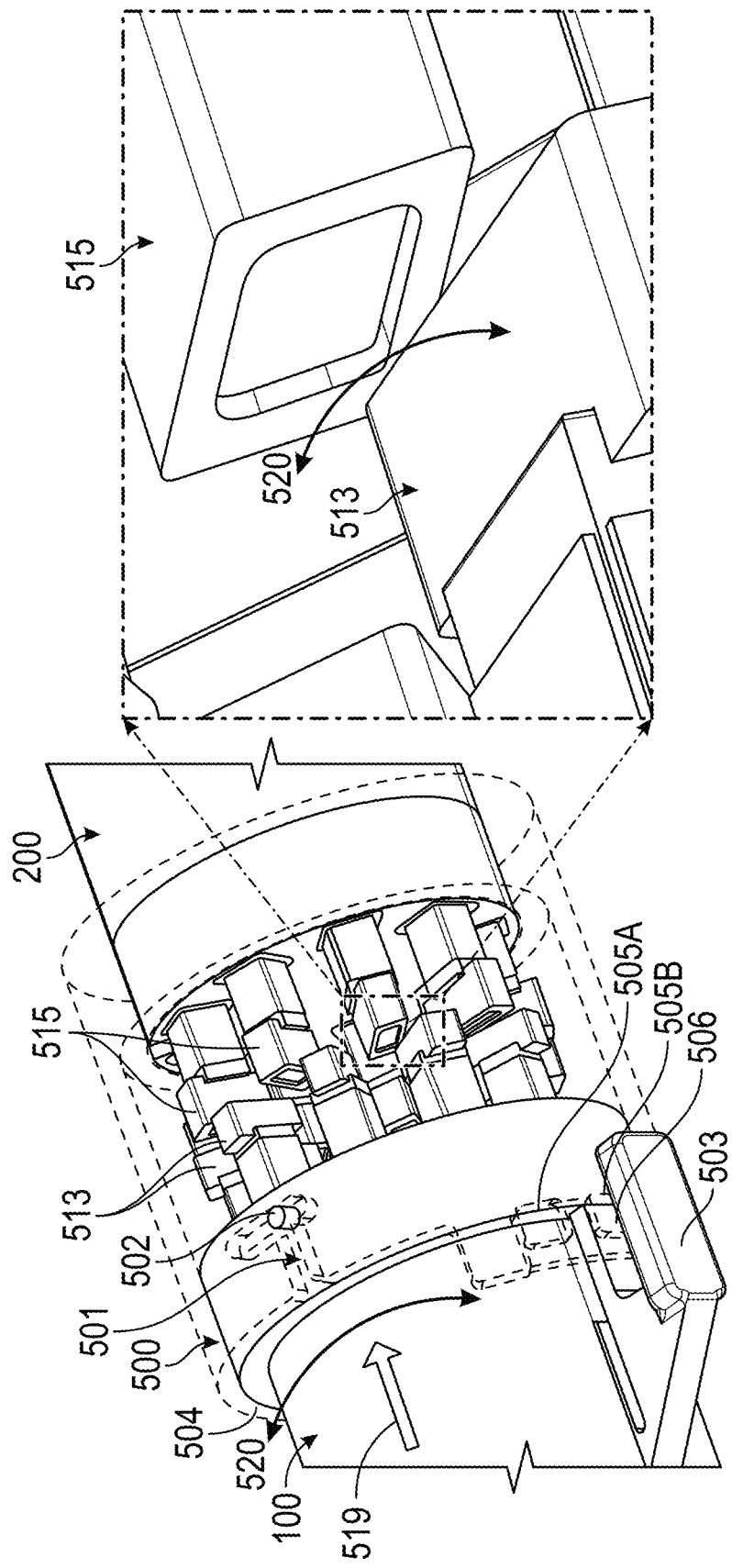

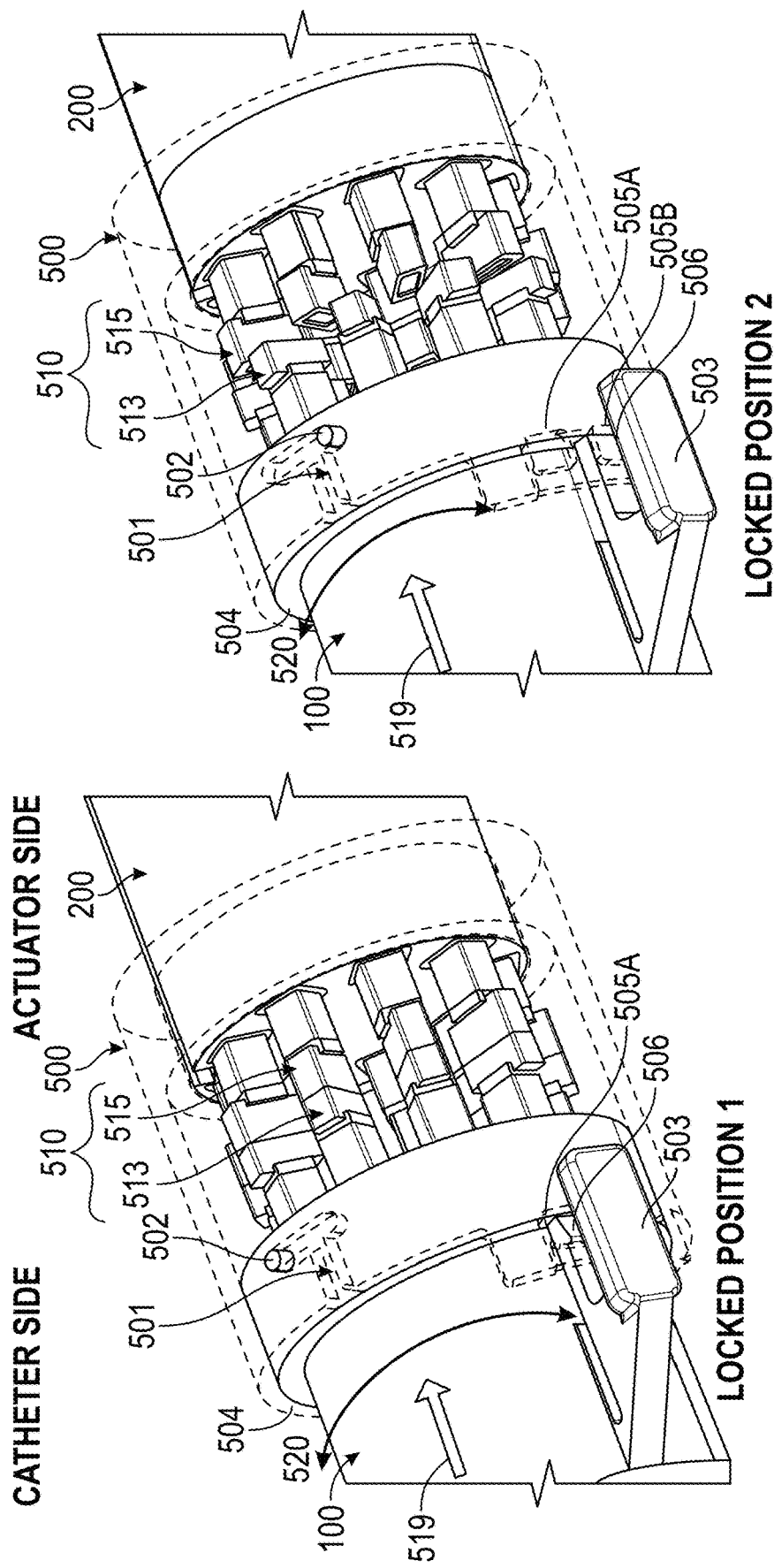

MAGNETIC CONNECTOR FOR STEERABLE MEDICAL DEVICE

CROSS-REFERENCE TO RELATED APPLICATIONS

The present application claims priority to U.S. provisional application 63/062,211, and U.S. provisional application 63/062,313, both filed on Aug. 6, 2020, the disclosures of the above-named applications are incorporated by reference herein in their entirety.

BACKGROUND INFORMATION

Field of Disclosure

The present disclosure generally relates to steerable medical devices. More particularly the present disclosure exemplifies various embodiments of a robotically steerable medical device capable of performing bending operations based on robotic actuation of drive wires. The steerable medical device is applicable to interventional medical tools and instruments, such as endoscopes and catheters, configured to navigate through intraluminal tortuous paths.

Description of Related Art

Medical steerable robots utilize drive wires to manipulate the shape of a steerable catheter, endoscope, or other surgical tool. In order to actuate the drive wires there is a drive mechanism, such as an actuator or a motor which provides an actuating force for the drive wires. The drive mechanism requires a form of connection between the drive wires and the actuator or motor. Current technology utilizes a variety of mechanical locking mechanisms such as clutches, latches or wedges for connecting the drive wires to the actuator or motor.

Examples of above technology are described in numerous patent and non-patent publications including, but not limited to, US 2007/0232856, U.S. Pat. Nos. 6,858,005 B2, 9,629,688 B2, 10,292,760 B2, and 10,722,296 B2. Most of these robotically controlled instruments (catheters or endoscopes) rely on pushing and/or pulling drive wires (also called tendons or tendon wires) to manipulate the shape of the tip of the instrument. A steerable catheter can contain a multiplicity of drive wires that manipulate different sections of the catheter body allowing for complex shapes. Often the catheter portion containing the drive wires is sterile and disposable, while the drive mechanism or actuator is part of capital equipment non-disposable and potentially non-sterile. Therefore, every time a steerable catheter is used each of the individual drive wires has to be connected to its corresponding actuator by a user. This process is cumbersome for the user, can potentially void the sterility of the catheter, and it is likely that the user could make an error and fail to properly lock one or more of the wires to the actuators causing a malfunction or potential damage to the instrument and/or the patient. To address such issues, there has been proposed a mechanical connector assembly that mechanically engages multiple drive wires with one or more force generators (actuators) with few movements. See, for example, U.S. Pat. No. 10,105,036 B2.

A mechanical assembly, as disclosed in the above U.S. Pat. No. 10,105,036 B2, typically locks the tool and the actuator together rigidly to a point where if there was excessive pull force, there would be no breakaway, and the tool could get damaged. More specifically, in robotic steerable catheters, drive wires can yield and/or fracture due to high pulling or compressive forces experienced during operation. A failure is particularly critical under compressive forces when the drive wire kinks at the tip and could herniate through the catheter wall, potentially damaging the instrument and/or harming the patient. Although, a catheter could be designed to fail at the mechanical junction hub so that patient exposure can be minimized, the drive wire would still be permanently damaged and the catheter would need to be replaced. Methods for avoiding drive wire failure include utilizing super elastic Nitinol wires, which can experience high strain without plastic deformation. Also, some catheter designs utilize pull only motion so that buckling/kinking is not an issue.

In the field of robotically actuated instruments, certain mechanical connections with breakaway safety are known from, for example, patent publications U.S. Pat. Nos. 8,337,783 B2, 8,251,084B2, and 9,114,540 B2, as well as in pre-grant patent publication US 2011/0018663 A1. However, these publications are unrelated to robotic catheter actuation by multiple drive wires; therefore they lack the ability to prevent compressive breakaway as well as breakaway between the actuator and the drive mechanism of a surgical instrument.

Accordingly, there is a need for robotically steerable catheters with a connector assembly having improved breakaway safety.

SUMMARY OF EXEMPLARY EMBODIMENTS

According to at least one embodiment of the present disclosure, there is provided an apparatus configured to establish a quick connection between a catheter body and an actuator by a plurality of magnetic connectors. The connection is made between multiple independent actuators and drive wires with a single motion. No additional action, such as latching, is required to create such connection.

According to the various embodiments disclosed herein, a robotically steerable medical apparatus comprises an elongate body (100) having a tubular opening (105) and a plurality of channels (104) arranged along a wall of the elongate body substantially surrounding to the tubular opening (105), the elongate body has a steerable section (103) and a non-steerable section (102); a drive wire (110) is arranged in at least one channel (104) and configured to manipulate the steerable section (103) of the elongate body (100); an actuator unit (310) is configured to apply an actuation force to the drive wire (110) arranged in each channel (104); a magnetic connector (510) is configured to magnetically couple the actuator unit (310) to the drive wire (110) via at least one magnet; and a controller (320) is configured to determine a connection status of the magnetic connector (510) and control the actuator unit (310) according to the connection status of the magnetic connector.

The magnetic connector 510 servers as a magnetic fuse comprising a pair of magnetically coupled shafts. The magnetic fuse comprises a cylindrical hub (611) with two plungers respectively attached to the shafts, one plunger on each side of the cylindrical hub, and two magnetic breakaway points. The two breakaway points of the magnetic fuse provide a fuse for a bi-directional breakaway force. The magnetic fuse allows breakaway to occur under a compressive force applied to the two shafts, which could prevent wire kinking and herniation. The magnetic fuse also allows breakaway to occur under a tensile force applied to the two shafts, which could prevent plastic deformation and/or fracture of drive wires. The magnetic fuse is configured to return to normal operation after recoupling. The magnetic fuse utilizes force feedback or other similar technique to sense disengagement and initialize a reengagement routine.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

A complete understanding of objectives, features and advantages of the present disclosure will become apparent to those skilled in the art from the following detailed description when taken in conjunction with the accompanying figures showing illustrative embodiments of the present disclosure, wherein like reference characters refer to like parts throughout the disclosure, and in which:

FIG. 7A and FIG. 7B respectively illustrate compressive breakaway and tensile breakaway features of a magnetic connector configured as a magnetic fuse, according to yet another embodiment of the present disclosure;

FIG. 10A, FIG. 10B, FIG. 10C, FIG. 10D and FIG. 10E illustrate various views of a magnetic connector hub 500, according to another embodiment of the present disclosure;

DETAILED DESCRIPTION OF EXEMPLARY EMBODIMENTS

Figure 1A:
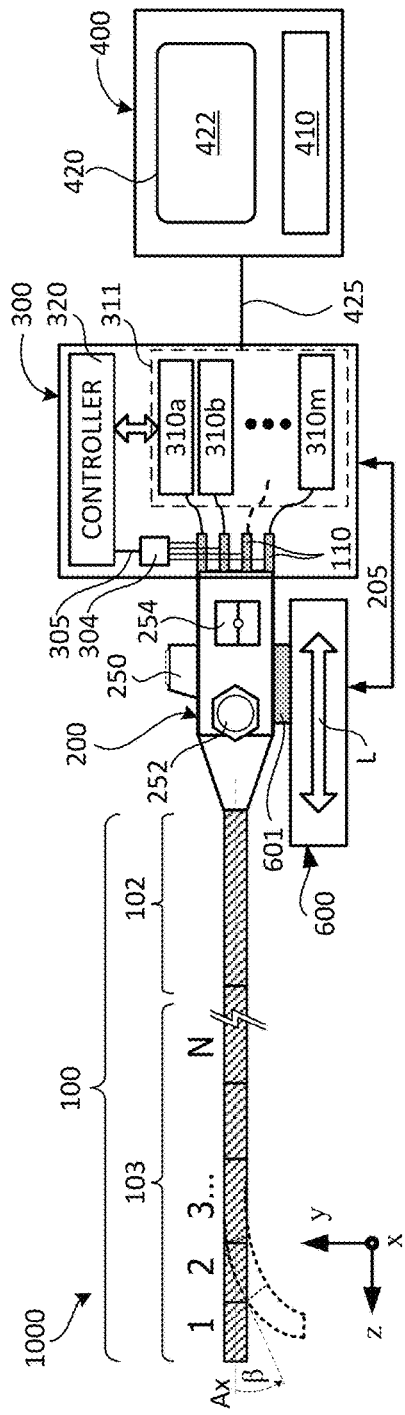
FIG. 1A illustrates a general structure of a continuum robot system 1000, according to one embodiment of the present disclosure.

Before the various embodiments are described in further detail, it is to be understood that the present disclosure is not limited to any particular embodiment. It is also to be understood that the terminology used herein is for the purpose of describing exemplary embodiments only, and is not intended to be limiting.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope and spirit of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to be inclusive of end values and includes all sub-ranges subsumed therein, unless specifically stated otherwise. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

Unless specifically stated otherwise, as apparent from the following disclosure, it is understood that, throughout the disclosure, discussions using terms such as "processing," "computing," "calculating," "determining," "displaying," or the like, refer to the action and processes of a computer system, or similar electronic computing device, or data processing device that manipulates and transforms data represented as physical (electronic) quantities within the computer system's registers and memories into other data similarly represented as physical quantities within the computer system memories or registers or other such information storage, transmission or display devices. Computer or electronic operations described in the specification or recited in the appended claims may generally be performed in any order, unless context dictates otherwise. Also, although various operational flow diagrams are presented in a sequence(s), it should be understood that the various operations may be performed in other orders than those which are illustrated or claimed, or operations may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "in response to", "related to," "based on", or other like past-tense adjectives are generally not intended to exclude such variants, unless context dictates otherwise.

The present disclosure generally relates to medical devices, and it exemplifies embodiments of an optical probe which may be applicable to a spectroscopic apparatus (e.g., an endoscope), an optical coherence tomographic (OCT) apparatus, or a combination of such apparatuses (e.g., a multi-modality optical probe). The embodiments of the optical probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object.

As it is known in the field of medical devices, the terms "proximal" and "distal" are used with reference to the manipulation of an end of an instrument extending from the user to a surgical or diagnostic site. In this regard, the term "proximal" refers to the portion (e.g., a handle) of the instrument closer to the user, and the term "distal" refers to the portion (tip) of the instrument further away from the user and closer to a surgical or diagnostic site. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes.

In the present disclosure, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers. An optical fiber has a generally transparent, homogenous core, through which the light is guided, and the core is surrounded by a homogenous cladding. The refraction index of the core is larger than the refraction index of the cladding. Depending on design choice some fibers can have multiple claddings surrounding the core.

Some embodiments of the present disclosure are directed to improving robotically-controllable endoscopes or catheters for application in minimally invasive surgical (MIS) procedures. MIS procedures involve the use of long rigid or flexible surgical instruments that are inserted into the body of a patient through small incisions or natural orifices. Today, there is wide range of well known endoscopic procedures both diagnostic and therapeutic purposes. An important aspect of using robotically driven catheters for MIS endoscopy is the ability to every time a catheter is connected to its drive mechanism each of the individual drive wires has to be connected to its corresponding actuator or motor correctly and in an efficient manner.

Figure 1B:
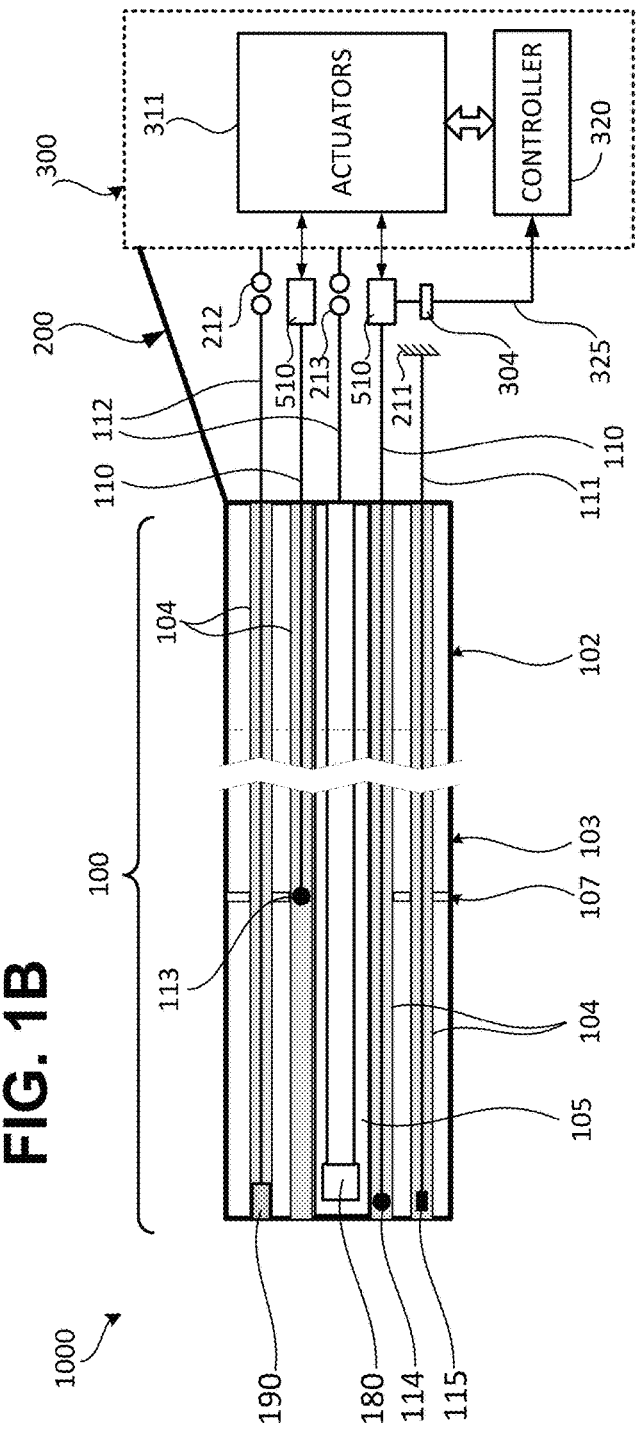
FIG. 1B illustrates in more detail electromechanical connections and magnetic connectors for interfacing a steerable instrument 100 to an actuator system 300.

<FIG. 1A-1B: System Configuration and Operation of a Steerable Medical Instrument>

A general configuration and operation principles of a steerable instrument 100 controlled by a continuum robot system 1000 is described with respect to FIGS. 1A and 1B. As used herein, the steerable instrument 100 refers to a steerable catheter or endoscope having a plurality of steerable sections which can be robotically manipulated by a drive mechanism of remote actuators. The robot system 1000 can include a continuum or multi-segment steerable instrument 100 configured to take a continuously curved geometry of at least a portion of an endoscopic probe, and to move the endoscope probe longitudinally along tortuous paths in a snake-like manner.

FIG. 1A illustrates a general structure of a continuum robot system 1000, according to one embodiment of the present disclosure. The system 1000 includes a computer system 400 (e.g. a system console), a robotic actuator system 300, and a steerable instrument 100 which is connected to the actuator system 300 via a connector hub or handle 200. In order from the proximal end to the distal end, and arranged along a longitudinal axis Ax, the steerable instrument 100 has a proximal section 102 which can be flexible but non-steerable and a distal section 103 which is steerable to form a continuously curved shapes. The distal steerable section 103 includes a plurality of bending segments 1, 2, 3 . . . N; these bending segments are formed by serially connected ring-shaped components. One or more of these bending segments can be actuated at the same time to bend and control a shape the steerable instrument 100 according to necessary applications. FIG. 1A, as an illustrative example, shows a portion of the steerable section 103 (drawn in dotted lines) which has been bent down by an angle $\beta$ relative to its original (non-actuated) position. The angle $\beta$ gives an angle in the y-z plane with respect to the catheter axis (Ax), while a second angle (not shown) can describe the motion of the instrument in the x-y plane around the catheter axis Ax. In this regard, the tip of the catheter can rotate through all 360 degrees on the x-y plane around the axis Ax, and up to about 90 degrees in the y-z plane. An angle greater than 90 degrees on the y-z plane would result in the looping of the catheter tip.

The steerable instrument 100 is a medical-grade steerable sleeve or sheath with sufficient length to reach a patient's organ depending on the specific application. The steerable instrument 100 forms an elongated tubular body coupled to, and controlled with/by a drive mechanism via connection hub or handle 200. Expressed in the x-y-z Cartesian coordinate system, the tubular body of the steerable instrument 100 has a tubular cross section lying in an x-y plane, and the longitudinal axis Ax lying along the z-axis perpendicular to the x-y plane. In other words, the distal end of the steerable instrument 100 points towards the z-direction, and is configured and dimensioned for insertion into a patient's body part either through a small incision or a natural orifice.

The actuator system 300 generally includes a controller 320 and an actuator unit 311 (drive mechanism). The controller 320 may include a proportional-integral-derivative (PID) controller or other digital signal processor (DSP) along with suitable software, firmware and peripheral hardware, as it is known to persons having ordinary skill in the art. PID or DSP-based controllers are generally dedicated integrated circuits; however DSP functionality can also be implemented by other circuits, for example, by using field-programmable gate array chips (FPGAs) or a computer processor. Therefore, in some embodiments, the actuator system 300 can be connected to a computer system 400 via a network connection 425. The controller or computer system 400, along with suitable software, firmware and peripheral hardware, operated by a microprocessor or central processing unit (CPU) 410 controls the functions of the continuum robot system 1000, as described in the remainder of this disclosure. Among other functions, the computer system 400 can provide a surgeon or other user with an image display device 420, such as an LCD or OLED display, and a graphical user interface (GUI) 422 with a touchscreen to interact and remotely operate the steerable instrument 100. Alternatively or in addition thereto, the actuator system 300 and/or handle 200 can be connected to a handheld controller, such as portable gamepad controller (not shown).

The actuator unit 311 includes a plurality of motors or actuators 310 (310*a*, 310*b* . . . 310*m*) equal to a plurality of drive wires 110 necessary for actuating and steering the instrument 100. According to an embodiment, nine individual motors or actuators 310 provide an actuating force (compressive or tensile force) to corresponding nine drive wires 110. All drive wires 110 are coupled, at the proximal end thereof, to individual motors or actuators 310. The drive wires 110 can be metal wires, for example, piano-type wires, stainless-steel wires, or nickel-titanium alloy (nitinol) wires. In the present disclosure, the type of actuator is not limited to any specific structure, and any of a direct current (DC) motor, a linear inductive motor, an ultrasonic motor, or the like can be used to displace (move) each drive wire 110 in a longitudinal or axial direction (a direction parallel to the longitudinal axis Ax). In the case of the DC motor, there needs to be a transformation from rotational motion to linear motion; for this, a lead screw or a ball screw mechanism is typically used. Other alternatives, such as ultrasonic and direct drive actuators, can be more advantageous. A benefit of an ultrasonic motor and a linear inductive motor is that these are both linear actuators and do not need mechanical conversion. An ultrasonic motor or a linear inductive motor can directly drive the drive wires without any gears or intermediate mechanisms. An advantage of driving the drive wires with such an actuator is the reduction of friction and other nonlinearities (e.g. avoiding mechanical slop in a lead screw mechanism).

The robotic actuator system 300 also includes and/or is connected to one or more sensors 304 (a sensor system). The sensor 304 can detect the physical connection of each drive wire 110 to the drive mechanism, such as motors or actuators 310. Sensors 304 can include a strain sensor and/or a position sensor for each drive wire 110. These sensors 304 serve to detect and/or measure compressive and/or tensile forces applied by the actuators 310 to actuate each drive wire 110. In the present disclosure, since a magnetic connector 510 is used to transfer force from the actuator 310 to a drive wire 110, the sensor 304 may further include a magnetic sensor, such as a Hall Effect sensor, capable of detecting an amount (or magnitude of) magnetic flux within the magnetic connector 510. The sensors 304 is operatively connected to the controller 320, and outputs a signal 305 corresponding to the amount of compressive or tensile force (a bending force) being applied to a drive wire 110. In an embodiment where the sensor 304 is a Hall Effect senor, the output signal 305 can correspond to an amount or magnitude of magnetic flux. The sensors 304 could also output a signal 305 corresponding to an amount of movement (a distance) of displacement for each actuated drive wire 110, at any given point in time during a procedure. The output signals 305 from the sensors 304 (strain sensor, position sensor, and/or magnetic field sensor) for each drive wire 110 are fed back to the controller 320 to control each actuator 310 and drive wire 110 individually with a feedback control loop 325. In this manner, each drive wire 110 can be actively controlled to implement appropriate shaft guidance for navigating the instrument 100 through intraluminal paths of a patient's anatomy.

The connection hub or handle 200 may include various mechanical, electronic, electrical, and optical components which serve to provide electromechanical interconnection between the steerable instrument too and the actuator system 300. For example, the handle 200 may provide mechanical, electrical, and/or optical connections, and a data/digital acquisition (DAQ) system for interfacing the steerable instrument 100 with the actuator system 300. The handle 200 may also provide an access port 250, one or more mechanical dials or knobs 252, and a user interface 254. The one or more control wheels or knobs 252 may be used to manually bend individual segments of the steerable section 103 in one or more directions. The access port 250 is used for insertion and extraction of tools into the tool channel 105, such as small forceps, needles, or electrocautery instruments and the like. The handle 200 is attachable to a robotic support platform 600 (e.g., a linear stage 601) to move the steerable instrument 100 in a linear direction L. The controller system 300 sends control signals to the support platform 600 and/or linear stage 601 via the handle 200 or/or an additional connection 205 such as a cable bundle.

As part of the user interface 254, the handle 200 may include one or more than one light emitting diode (LED) for providing operational status of the robotic steerable instrument 100 to a user. In an embodiment, the LED may include, for example, different light colors for respectively indicating normal operations (green light) and abnormal operations (red light). Alternatively, the LED may include blinking codes, for example, to indicate a type of abnormal operation. In addition, the user interface 254 may include an emergency on/off switch to manually stop actuation of the steerable instrument 100, in the event of an emergency.

FIG. 1B illustrates in more detail relevant parts of the steerable instrument 100. The steerable instrument 100 has an elongate flexible shaft (elongate body) also referred to as a sleeve or sheath. Along the sheath's length, there are channels extending from the proximal end to the distal end along (parallel to) the longitudinal axis Ax. Among these channels, the sheath may include one or more tubular openings 105 extending along (typically inside) the sheath, and a plurality of wire conduits 104 extending along (typically within) the wall of the sheath. The one or more tubular openings 105 serve as tool channels to allow access for medical tools (end effectors) to be delivered from access port 250 to the distal end of the steerable section 103. The tubular opening 105 may also be used for sending or retrieving liquid or gaseous substances (e.g., air or water) to a target area, or for passing optical fibers and/or electric wires. Furthermore, the one or more channels 105 may be used for inserting one or more of a medical imaging device 180, such as an endoscope camera or a fiber-based imagining probe. An example of an endoscope camera includes, but is not limited to, a chip-on-tip (COT) camera, such as a camera with a miniature CMOS sensor and an illuminator arranged at the tip of the endoscope. Examples of fiber-based imaging probes include, but are not limited to, a near infrared auto-fluorescence (NIRAF) imaging probe, a spectrally encoded endoscopy (SEE) probe, an intravascular ultrasound (IVUS) probe, an optical coherence tomography (OCT) imaging probe, or a probe with a combination of two or more of these devices.

The steerable instrument 100 is configured to provide flexible access to intraluminal target areas with one or more than one bending curves to reach the intended target area located near (at a working distance from) the distal end of the instrument. Desirably, the steerable instrument 100 is capable of retaining torsional and longitudinal rigidity so that a user can control end effectors and/or imaging devices located at the distal end of the sheath by remotely maneuvering the distal end of instrument 100 from the control knobs 252, the actuator system 300 and/or computer system 400. In order to provide such steerable functionality, the steerable instrument 100 is actuated with a plurality of drive wires 110 which are arranged inside the wire conduits 104 along (typically within) the wall of the sheath. Some of the drive wires 110 are anchored at the distal end of the sheath using wire anchors 114, and other drive wires 110 can be anchored at certain predetermined distances from the distal end using wire anchors 113. In some embodiments, the steerable instrument 100 may include one or more support wires 111 (tendon wires). Support or tendon wires 111 can be optional at some locations of the steerable section, and are typically anchored at the distal end of the sheath with wire anchors 115, and can be mechanically grounded (fixedly attached) to a support section 211 (e.g., the chassis, a mechanical spring, etc.,) of the handle 200.

In one exemplary embodiment, the steerable instrument 100 with six drive wires 110 may have two pairs of drive wires 110 (i.e., four drive wires) anchored by wire anchors 113 in the midsection of the sheath (e.g., at one or more inflection points 107), and another pair of drive wires 110 (two drive wires) could be anchored by wire anchors 114 at the distal end of the sheath. In this manner, the steerable instrument 100 can have at least two (i.e., two or more) steerable sections controlled by 3 pairs of antagonistic drive wires no, where each wire extends through a separate wire conduit 104. According to one embodiment, the steerable instrument 100 can have 3 locations with anchored drive wires 110, and two locations with anchored support wires 111. The most distal anchor point has 3 drive wires 110 and 3 support wires 111. The "middle" anchor point has 3 drive wires and no support wires. And the most proximal anchor point has 3 drive wires and 3 support wires.

The wire conduits 104 allow anchorage and/or passage of drive wires 110 used for steering (bending or twisting) at least one segment or section of the sheath. In addition, at least some wire conduits 104 can be used to pass one or more electrical cables 112. Electrical cables 112 are configured to establish an electrical connection between an electronic device arranged at or within the steerable section 103 and a signal processing circuit located outside of the proximal end of the instrument. For example, an electrical cable 112 can be used to connect one or more electromagnetic (EM) sensors 190 to first electrical terminals 212 located at the handle 200. In some embodiments, the tubular opening 105 can also be used to pass additional electrical cables 112 which can connect an imaging device 180 to second electrical terminals 213 also located at the handle 200.

At the proximal end of the instrument 100, the handle 200 is configured to provide a mechanical linkage and an electromechanical interface between the steerable instrument 100 and the actuator system 300. According to the present disclosure, the handle 200 provides a plurality of magnetic connectors 510 (one connection for each of the drive wires 110) so actuators 310 of the actuator unit 311 can mechanically actuate each drive wire 110. Each magnetic connector 510 is in operative connection with the one or more sensors 304 to create a feedback loop 325 (based on a signal 305) for controller 320. The controller 320 is used to electronically control the operation (movement) of each drive wire 110 based on a driving force applied to each drive wire 110. A "driving force" is understood as one or more of tensional, compressive, and/or torsional forces applied to the drive wire in order to actuate the steerable instrument 100. In some embodiments, the term "bending force" is understood as a tensional force or compressive force applied to the drive wire to bend at least one segment of the steerable instrument 100.

Figure 2:
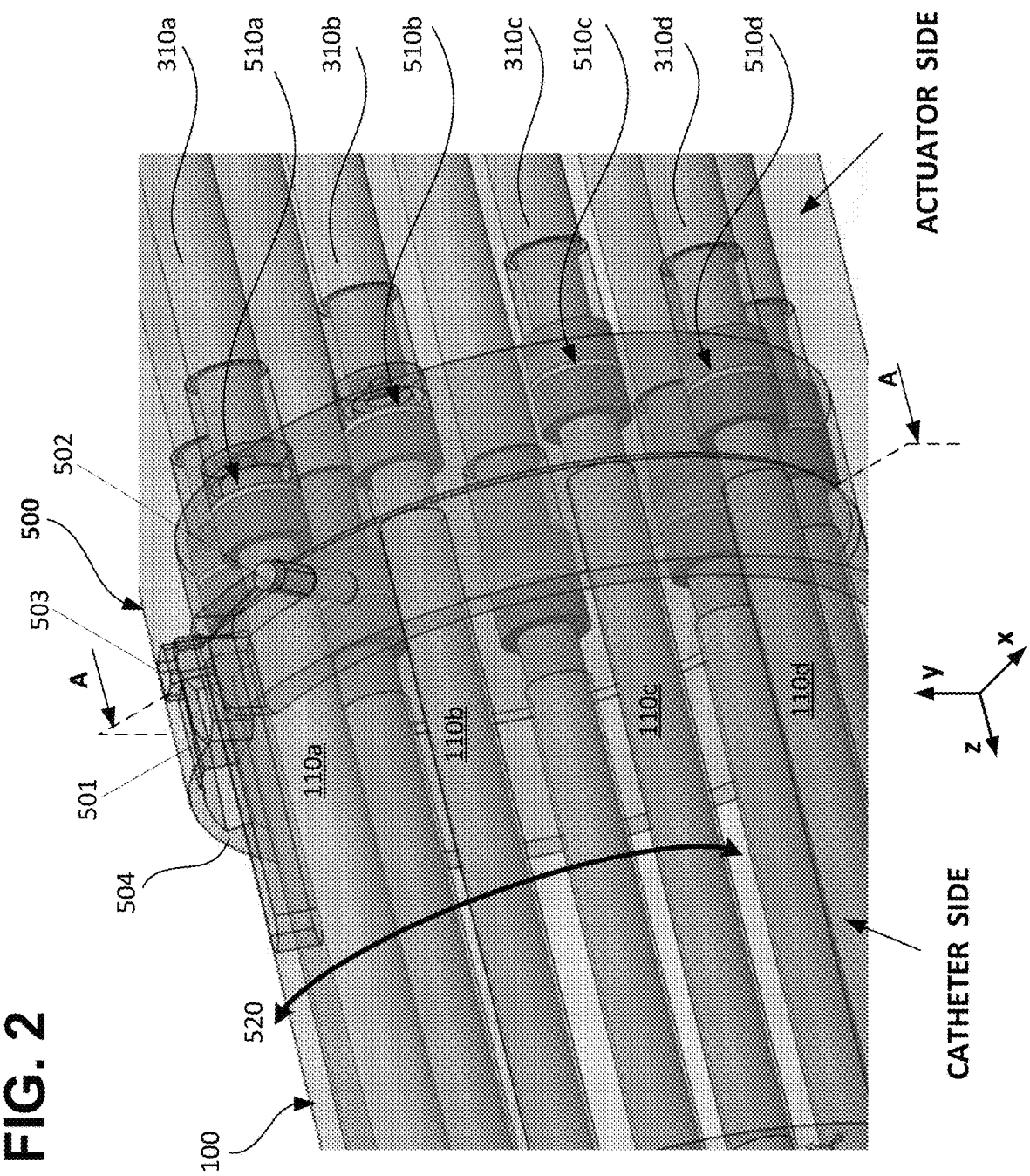
FIG. 2 illustrates an example embodiment of a connection hub 500 comprised of plurality of magnetic connectors 510.

<FIG. 2: Magnetic Connector Hub>

As mentioned above, in order to actuate the drive wires 110 there must be a drive mechanism, such as a motor or actuator 310, which requires a form of connection, such as an electromechanical connection between the drive mechanism and each of the drive wires. FIG. 2 illustrates an exemplary embodiment of an electromechanical connection hub implemented by a plurality of magnetic connectors 510 arranged in a connection hub 500, according to the present disclosure.

As shown in FIG. 1A and FIG. 1B, the general structure of the system 1000 requires an actuator system 300 to provide a driving force to the steerable instrument 100. The steerable instrument 100 has at least one bending section, and receives the driving force via drive wires 110 (control wires) that rely on push/pull motions to manipulate the bending section(s). A connection hub (e.g., arranged in the handle 200) allows the actuator system to manipulate the individual drive wires.

FIG. 2 illustrates an exemplary embodiment of a connection hub 500, according to the present disclosure. According to this embodiment, the connection hub 500 includes a plurality of magnetic connectors 510 (510a, 510b, 510c, etc.) arranged around a central axis of a cylindrical housing 504. The cylindrical housing 504 is provided on the actuator side of the actuator system and serves to enclose the magnetic connectors 510. Each magnetic connector 510 is configured to magnetically couple one actuator 310 to one of the catheter drive wires 110. To facilitate ease of mechanical connection between the proximal end of steerable instrument 100 and the connection hub 500, the housing 504 includes a keyway 501 and the steerable instrument 100 includes a guiding pin 502. When the proximal end of the steerable instrument 100 slides into the housing 504, the guiding pin 502 follows along the keyway 501, and the plurality of magnetic connectors 510 magnetically couple the plurality of actuators 310a, 310b, 310c, 310d, etc., of the actuator unit 311 to the plurality of catheter drive wires 110a, 110b, 110c, 110d, etc., of the steerable instrument 100.

Figure 3:
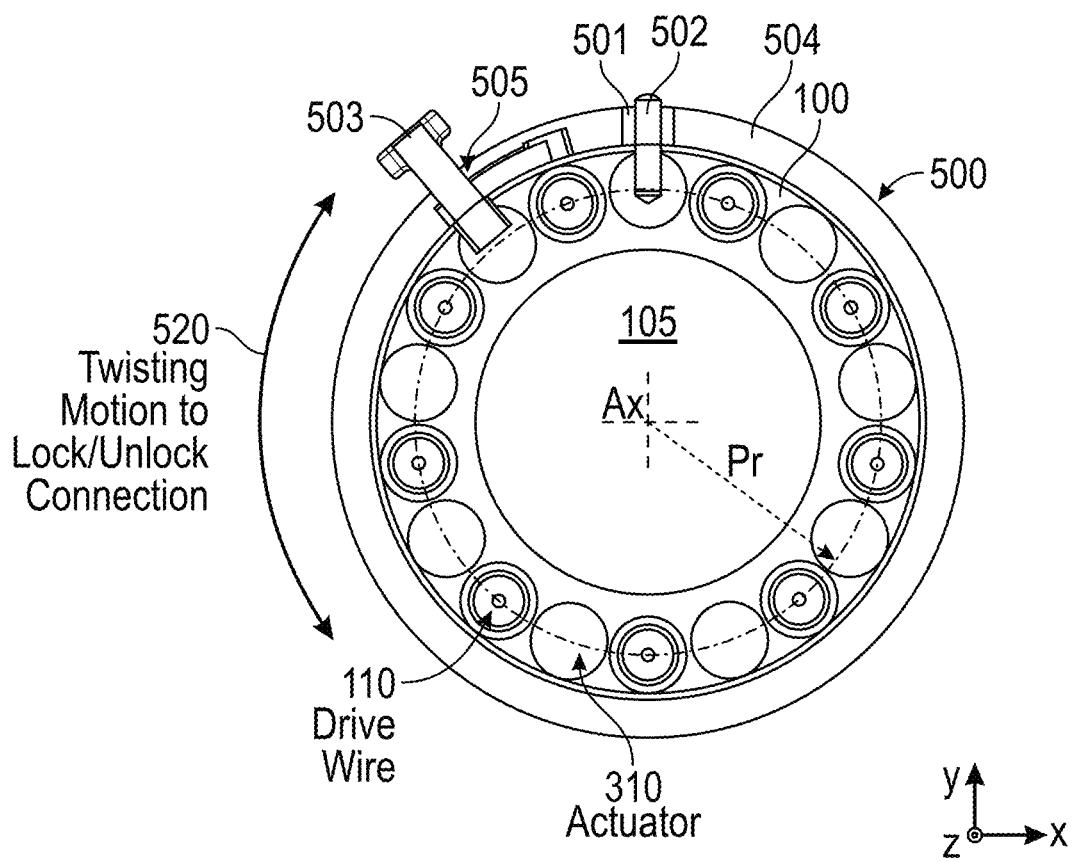
FIG. 3 shows a cross-sectional view of the connection hub 500, illustrating an example of a single step connecting action for mating a plurality of actuators 310 to a plurality of drive wires 110.

FIG. 3 illustrates a cross-sectional view of the connection hub 500 taken along lines A-A of FIG. 2 in a direction from the proximal end towards the distal end of the steerable instrument 100. This analogous to saying that the cross-sectional view A-A shown in FIG. 3 is seen in a direction from the actuator side to the catheter side. The plurality of drive wires 110 and actuators 310 (nine of each in this example) are arranged in a circular fashion around the instrument central axis Ax at a pitch radius (Pr) so as to surround the tool channel 105. A maneuver for attaching the drive wires 110 to the corresponding actuators 310 via the connection hub 500 can be completed by a single action of a user, who performs an "insert and twist" motion. Specifically, during the connection process, the user first inserts the proximal end of the steerable instrument 100 (a catheter, an endoscope, or the steerable sheath with or without a tool) into the housing 504 of connection hub 500 utilizing a guiding mechanism such as the keyway 501 and the guiding pin 502 for proper alignment (see FIG. 2). At this point, after linear insertion of the steerable instrument 100 into the housing 504, the actuators 310 and magnetic connectors 510 are not yet aligned with the drive wires 110 (see FIG. 3). Once the maximum depth of insertion is reached, the user performs a twist motion in a direction of arrow 520, aligning the actuators 310 to the corresponding drive wires 110, and placing the connection hub 500 in a locked position. In the locked position, a lock 503 (e.g., a spring loaded beam/ knob) aligns with or snaps into and opening 505 to prevent accidental disengagement.

The controller 320 (or CPU 410) then senses that the user has performed the manual connection and begins an engagement procedure where the actuators 310 move forward (in the z-direction), and magnetic coupling occurs between each actuator 310 and a corresponding drive wire 110 via each magnetic connector 510. To disconnect the user pulls the lock 503 to free the pin 502, does the opposite of connecting by twisting and pulling the body of the steerable instrument 100. In the removal process no procedure is required by the controller. As soon as the user twists and pulls the steerable instrument from the actuator mechanism, the magnetic connection is broken, and the sensors 304 stop any communication between the actuator system 300 and the steerable instrument 100.

According to another embodiment, only the magnetic coupling breaks away at a threshold force without the instrument 100 being removed from the connection hub 500. The threshold force is determined by the size and strength of the magnet(s) selected. This is a unique feature in that the magnetic breakaway prevents damage to the catheter/tool and/or patient when at least one of the drive wires 110 in the catheter body experiences an excessive bending force. This is an important feature of the magnetic coupling as it adds a safety mechanism and helps protect the patient and/or the steerable instrument. In addition, since the coupling is magnetic, the coupling can be rigid and thus can prevent backlash or slack in the drive wires. Since the magnetic connection does not require any electrical induction and each magnet is individually enclosed in a separate casing, the magnetic coupling can be broken at any point in the catheter travel making it advantageous for easy removal and emergency disconnection. This works because the hub twisting mechanism for connection and disconnection between the catheter and the actuator unit is separate from the drive wire actuator mechanism. There is no possible scenario where the drive wire slides will interfere with the adjacent actuator slide due to spacing.

<FIG. 3: Single Action Connection>

In one particular embodiment, e.g., as shown in FIG. 2, there are 9 actuators 310 and 9 catheter drive wires 110 that are magnetically coupled by 9 magnetic connectors 510. The coupling breaks away at a force of about 20 Newtons (N) in the actuation direction. To connect the actuators to the drive wires, the actuator side must be commanded to move all of the actuators to the rear most position (home position), or else the connection may not work. If the actuators are not in the rear most position, they can interfere with the drive wire slides since the actuator is in a more forward position than the drive wire. Therefore during the twisting engagement action, the actuator slide must be positioned to the rear most position relative to the drive wire slide. Once the user has inserted and twisted the catheter body into the lock position, the actuators 310 are commanded by the controller 320 to move forward, and then the magnetic coupling engages. To disconnect the actuator mechanism from the drive wires 110, torque is applied and the magnet 515 for each magnetic connector 510 slides laterally (radially) to the position shown in FIG. 3. As used herein "torque" is understood as a force that produces or tends to produce torsion or rotation of an object about an axis or a pivot point. In the present case, the torque necessary to disconnect the actuator mechanism from the drive wires 110 can be applied manually by the user, or it can be applied automatically by a torque mechanism, such as a spring loaded cam or pin configured to apply torque at certain amount of tension or pressure.

Figure 4:
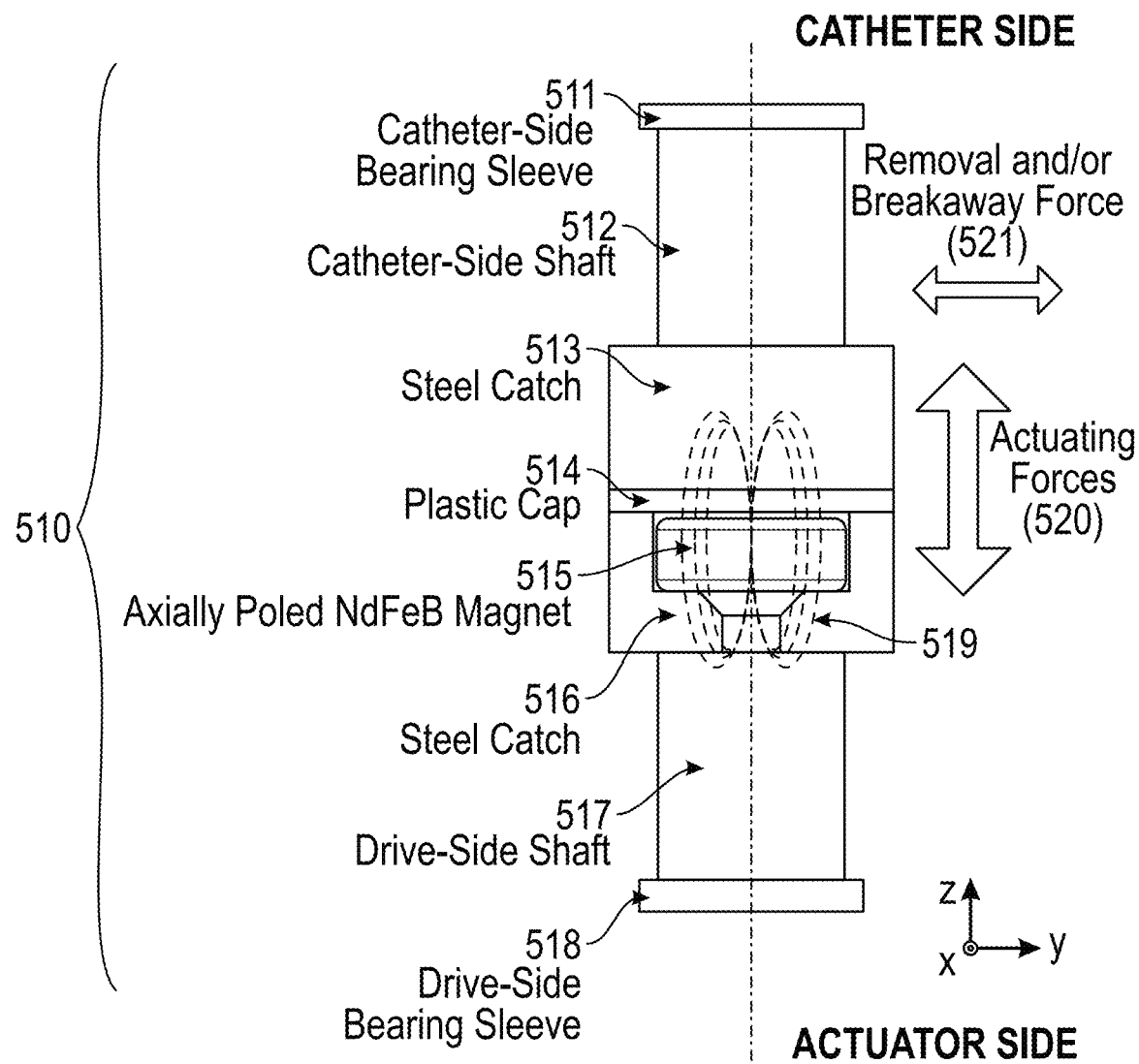
FIG. 4 illustrates certain components and forces of a magnetic connector 510 configured to magnetically connect a drive wire 110 to an actuator 310, according to a first embodiment.

<FIG. 4: Magnetic Connector and Actuating Forces>

FIG. 4 illustrates an example embodiment of a magnetic connector 510 and the directions of actuation force 522 and removal force 521 exerted in the magnetic connector 510 for operating a single drive wire no with a corresponding actuator 310. Specifically, as illustrated in FIG. 4, the direction of the actuating force (push or pull force) 522 is substantially parallel to the lengthwise direction of the instrument 100 and/or drive wire 110. On the other hand, the direction of a removal force 521 (for disengaging the magnetic junction) is substantially perpendicular (lateral) to the lengthwise direction of the drive wire 110. As mentioned above, to disconnect the actuator mechanism from the drive wires 110, each actuator (310a, 310b, 310c . . . 310m) can be placed to a home position, and then torque is applied either manually by the user, or by the actuator 310, and the magnet for each magnetic connector 510 slides laterally to the position shown in FIG. 3.

Therefore, it is important that each magnetic connector 510 is made of appropriate components that can withstand the actuation force 522 and removal force 521 without affecting accuracy of wire movement and without affecting tensile or compressive forces (i.e., without creating slack) during actuation. To that end, each magnetic connector 510 includes a catheter-side bearing sleeve 511, a catheter-side shaft 512, a catheter-side steel catch 513, a plastic cap 514, a ring-shaped or disc-shaped or cylindrical-shaped axially poled rare-earth magnet 515, an actuator-side steel catch 516, an actuator-side shaft 517, and an actuator-side bearing sleeve 518. Here, it should be noted that the catheter-side steel catch 513 may be formed of any magnetically permeable material (e.g., a ferrous material) and is part of, or is directly connected to, the drive wire 110. Similarly, the actuator-side steel catch 516 is part of, or is directly connected to, the actuator 310.

By "axially" poled magnet is understood a magnet system which is axially polarized in the direction defined by the North-South pole designation, such that the magnetic field is distributed substantially perpendicularly to the front face of the target and whose magnetic dipoles consequently are substantially perpendicular to said surface. The entry/exit faces for the magnetic field, which face the target, are therein substantially parallel to the target front face. By "axial" components of the magnetic field are understood components which are perpendicular to the target front face, or, in the case of a nonplanar target front face, perpendicular to the tangential plane at the target front face, at the front face point closest to the spatial point considered with reference to the magnetic field.

Magnet 515 may be formed of a rare-earth material such as neodymium iron boron (NdFeB) or other similar materials, and the magnet or magnets may be arranged with common poles on the inside diameter and common poles on the outside diameter. A schematic representation of the magnetic field of magnet member 515 is represented by reference numeral 523.

The plastic cap 514 secures the magnet 515, and provides a low friction surface for lateral breakaway on the actuator side. The plastic cap 514 may be formed of molded semi-rigid plastic material, such as nylon or similar, applied to the end surface of the actuator-side steel catch 516, or to the end surface of the catheter-side steel catch 513, or both. In at least one embodiment, the plastic cap 514 can have the following dimensions of about 8 mm to 12 mm outer diameter (OD) and 0.05-1.00 mm thickness, and it can be made of the following materials nylon, HDPE, PTFE, PP, or the like. Altering the thickness of the plastic cap 514 can allow the breakaway force to be fine-tuned to satisfy specific needs or requirements. This way the breakaway force can easily be changed to match the design of the catheter. For instance, the breakaway force should be larger than the pull/push force required to get the desired bend, but lower than the yield/kinking force of the catheter. According to one embodiment, the magnet 515 is provided only on the actuator side of the magnetic connector 510, and not on the catheter-side. One reason for not providing the magnet 515 on the catheter side is that the catheter would be disposable. Upon disconnection from the catheter body, the magnets 515 can be protected by a cover or sheath of non-magnetic material where they are recessed so foreign objects will not be attracted to the magnetic field when a tool is not attached. A cover can be designed with a self-closing mechanism, such that the cover slides over or otherwise encloses the magnets immediately after the catheter is removed from the connection hub 500. This is an important safety feature as the magnetic attraction could potentially cause harm to the user.

Figure 5:
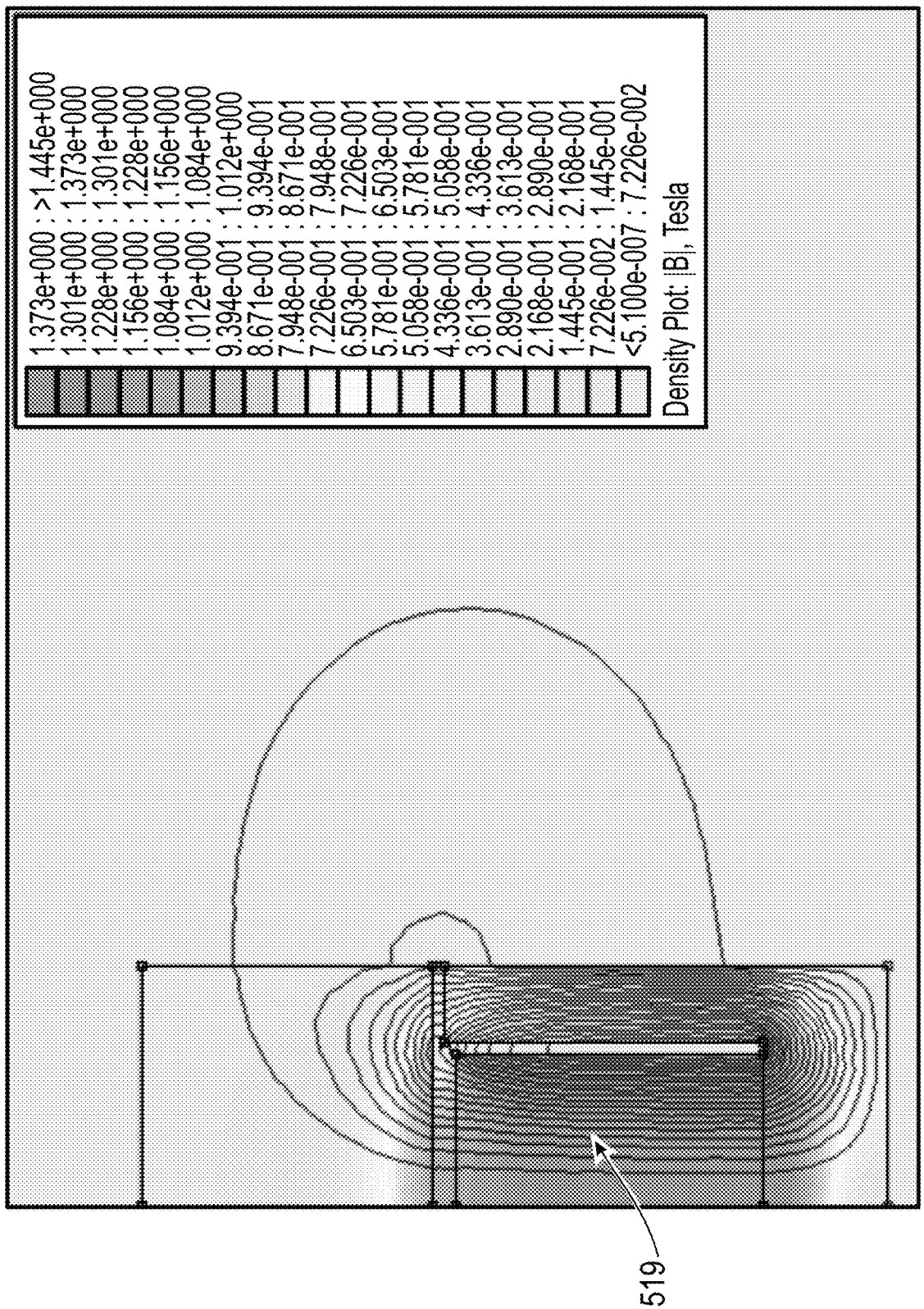
FIG. 5 is a graph showing a magnetic field of an axially poled magnet of the magnetic connector 510; the magnetic field was calculated using two dimensional magneto-static finite element analysis.

<FIG. 5: Magnetic Engagement and Disengagement>

FIG. 5 illustrates a graph of a magnetic field (flux density plot) 523 exerted by a single magnet 515 of the magnetic connector 510 shown in FIG. 4. According to one or more embodiments, the engagement force exerted by magnetic field 523 was calculated using two dimensional magneto-static finite element analysis. In the illustrated embodiment shown in FIG. 4, magnetic attraction between permanent magnet member 515 and the catheter-side steel catch 513 provides for an attraction of substantial force that requires a tension force greater than 20 N to separate or pull apart the actuator-side steel catch 516 from the catheter-side steel catch 513. In some embodiments, the attraction force may require more or less than 20 N to separate the steel catch members 513 and 516. However, after the steel catch members 513 and 516 have been separated as a result of the axial tension force, it will be appreciated that the magnetic coupling force provided by the magnet 515 allows a convenient means for reconnecting the steel catch members with only a small force (or a minor movement) because the magnetic attraction will pull back the catheter-side steel catch 513 towards the actuator-side steel catch 516. In order to achieve a 20 N engagement force, it was determined that an axially poled cylindrical magnet having 5/16 inch diameter was required. To achieve a 12 N engagement force, an axially poled cylindrical magnet having a ¼ inch diameter was required. With the magnetic flux required for the 12 N or 20 N engagement force, another important design feature of the magnetic connector 510 is that there is no magnetic flux saturation where magnetic fields would enter the vicinity of other actuators or potentially outside interferences. This protection is obtained by creating a steel loop around the magnetic flux that closes the loop of the magnetic path so that the flux density outside each single connector 510 is less than 0.1 Tesla. In order to achieve this, according to one embodiment, a 20 N connection hub 500 requires a 12 mm overall diameter, while a 12 N connection hub 500 requires a 10 mm overall diameter.

To calculate the lateral removal force 521 (to break away the magnetic coupling) it is necessary to know the coefficient of friction between the material of the plastic cap 514 (e.g., about 0.05-0.2 for PTFE and Steel) and that of the steel catch 516. According to a prototyped device construed by the inventor(s) herein, the result for the friction coefficient between plastic cap 514 and the steel catch 516 was approximately 0.2. Therefore, given the number of actuators 310 in a connector hub 500, and the pitch radius (the distance between the contact surface and the center of twisting rotation) of the actuators, it is also possible to calculate the required minimum removal torque. The torque can be calculated by multiplying the clamping force (magnetic coupling force), coefficient of friction, pitch radius, and number of actuators. A 20 N clamping force, 0.2 coefficient of friction, 30 mm pitch radii, and 9 actuators would result in a removal torque of approximately 1 N*m.

As explained previously with respect to FIG. 1A-1B, a sensor 304 can provide a force feedback signal 305 for each actuator 310 to sense when at least one drive wire 110 has been disengaged from its corresponding actuator 310. The controller 320 can be programed with appropriate algorithms to initiate reattachment between the actuator and the drive wire. The design of the connection hub 500 may use a calibration or homing algorithm, utilizing force feedback to make the initial magnetic connection between the actuator 310 and drive wire 110 via the magnetic connector. Linear bearings can be used to absorb lateral force so there are not transfers to the catheter drive wire causing damage. Linear bearings can be sliding shaft style, recirculating ball ways, or similar linear bearing technology. The linear bearings' function is to allow motion in one direction while restricting it in another. To that end, linear bearings are free to move in the desired direction of motion (in this case, the drive wire push or pull direction), while they are stiff in the lateral directions (the direction of twist). Therefore the force from the removal torque is not transferred to the catheter wire but instead to the bearing mechanism. In the case of a recirculating ball way, there are hardened steel ball bearings between the moving part and the stationary part. The ball bearings roll in the direction of desired motion, and resist force in the lateral direction. The plastic cap 514 in each magnetic connector 510 has a compliant nature which allows for minor misalignment between the catheter-side shaft and the actuator-side shaft. An alternative embodiment could utilize a separate coupling mechanism to deal with the issue of misalignment. For example, a commercially available coupling component that allows for the connection of two moving shafts that are not perfectly aligned could be used. This type of coupling mechanisms are stiff in the direction of motion, allowing for rigid transfer between the moving parts, while they are flexible in other directions to allow for dynamic displacement due to misalignment.

Due to friction in the catheter and inherent forces required to bend the various sections of the catheter body, there is a minimum force that the actuator will experience any time that it is connected to the catheter. When the force feedback reading drops below a certain threshold an engagement routine will be executed to re-engage the drive wire. The routine slowly advances the actuator until it reads a jump in feedback force, thus ensuring connection.

Figure 6:
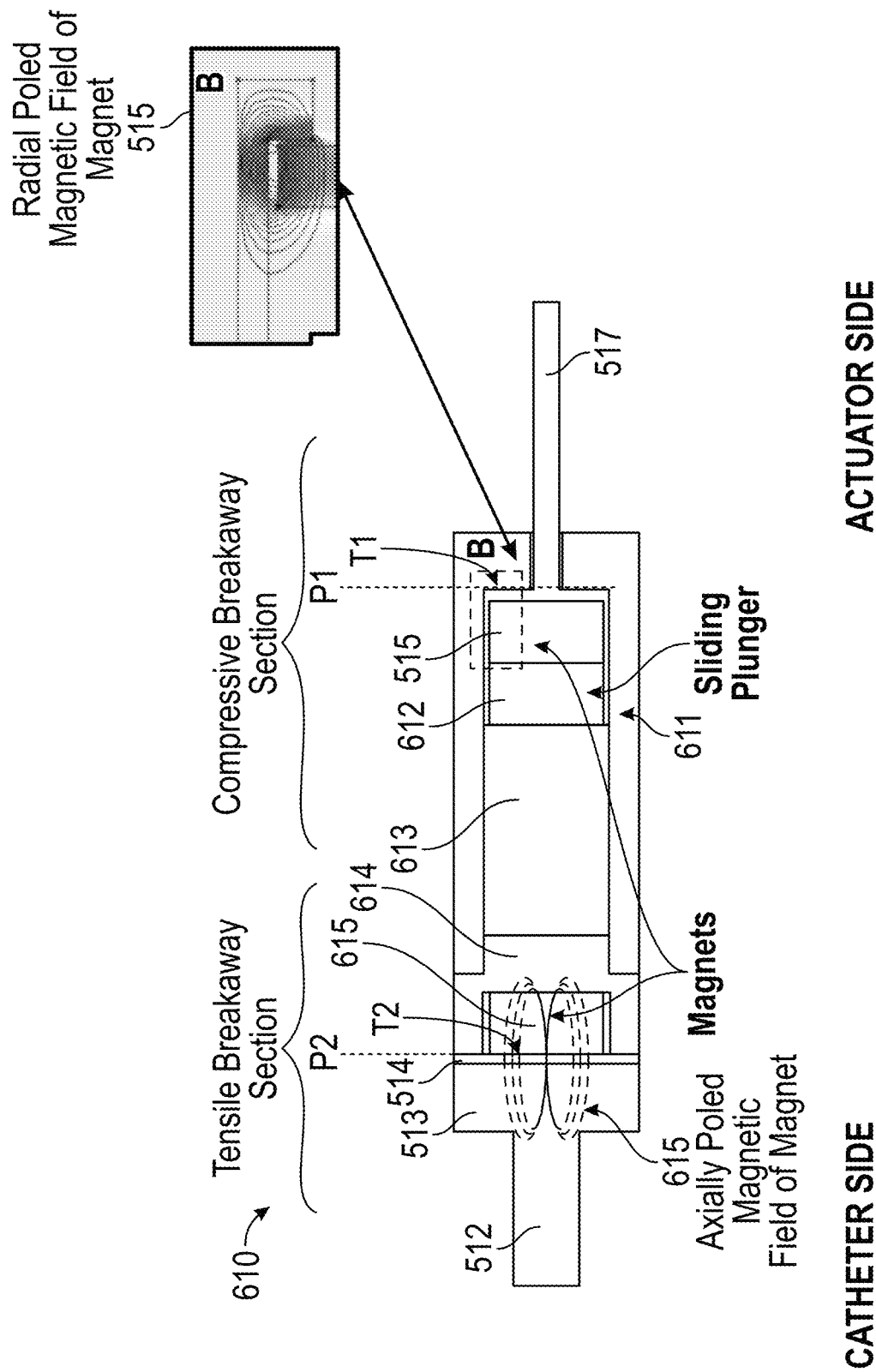
FIG. 6 illustrates an exemplary magnetic connector 610 configured with breakaway features, according to another embodiment of the present disclosure.

<FIG. 6-7: Magnetic Breakaway>

As previously mentioned, the catheter drive wires 110 may fail (yield and/or fracture) due to high driving force (tensile and/or compressive forces) experienced during operation. According to at least one embodiment of the present disclosure, the connection hub 500 can operate as a magnetic fuse creating a breakaway safety feature for the connection between the drive mechanism and the drive wires 110.

In general, either during insertion or retraction of the steerable instrument 100, the center line of the bodily lumen is the desired trajectory to be followed during active control of the steerable instrument. To that end, conventional steerable instruments, such as guided catheters or endoscopes, have attempted to implement various concepts of shaft guidance with the goal of forcing the flexible shaft of the steerable instrument to keep to the desired trajectory. In one example described by publication US 2007/0135803, which is incorporated by reference herein for all purposes, the steerable instrument is advanced through a lumen while sensors measure the insertion depth of the shaft-guide and the angulations of user-controlled steerable tip segments to obtain trajectory information. The trajectory information is stored in a memory of the system. After a short advance in insertion depth, the shape of the steerable instrument is corrected by adjusting (rotating or bending) segments of the instrument in such a way that the new shape closely matches the desired trajectory. This process is repeated until the tip of the instrument reaches a target area. However, most steerable medical instruments still need support from the surrounding anatomy to follow the desired trajectory. In particular, when external disturbances (external forces) are applied to the steerable instrument, it is difficult to keep the steerable instrument on the desired trajectory because the bent section or the tip of the steerable instrument can become stuck on the patient's anatomy and may hinder appropriate navigation. Similarly, during retraction of the steerable instrument, the guidance system is generally inactive, which places the steerable instrument in a non-controlled (passive) state. However, the steerable instrument can contact the patient's anatomy and this can exert a certain bending force on the instrument and cause discomfort and/or pain to the patient.

According to the present disclosure, the magnetic connector hub 500 can be configured as a magnetic fuse which consists of a magnetically coupled shaft that disengages at a driving force greater than a maximum operating force and lower than a failure force during an insertion procedure. In addition, the magnetically coupled shaft can disengage after detecting a predetermined amount of bending force during a withdrawal procedure. According to the embodiment shown in FIG. 4, breakaway of the magnetic coupling occurs under significant bending force experienced by the drive wire 110, e.g., external forces that cause the steerable instrument 100 to get stuck along the tortuous pathways of a bodily lumen.

According to another embodiment, the magnetic breakaway includes a two stage design that works for both compressive and tensile forces. For tensile forces greater than a maximum operating force, the magnetic coupling breaks away allowing for the steerable instrument to become compliant. Thereafter, the magnetic coupling can be easily reengaged with actuator motion based on programmed algorithms. For tensile disengagement (magnetic disengagement due to excessive tensile force) the actuator 310 will move forward (towards the distal end of the catheter) to reengage with the drive wires 110, while for compression disengagement (magnetic disengagement due to excessive compressive force) the actuator will move backwards (away from the proximal end of the catheter). In some embodiments, force feedback can be used to cause disengagement and/or reengagement at a certain levels of dynamic force due to friction and bending. For example, after disengagement, when the force drops below an operating force the controller will initiate an algorithm to reengage and resume normal operation.

FIG. 6 illustrates an embodiment of a magnetic connector 610 that can operate as a magnetic fuse configured to provide both compressive and tensile breakaway safety. As shown in FIG. 6, the magnetic connector 610 includes two magnetic coupling sections, one for compression and one for tension. The two coupling sections can be provided both on the actuator side of the connection hub 500 similar to the previous embodiment. However, in alternate embodiments, the two magnetic coupling sections can be provided on the instrument side (i.e., on the catheter side). In further embodiments the two magnetic coupling sections could even be divided and provided on the actuator side and on the instrument side (i.e., one coupling section on each side).

In the embodiment shown in FIG. 6, the magnetic connector 610 includes a catheter-side shaft 512, a catheter-side steel catch 513, a plastic cap 514, an actuator-side shaft 517, and a first magnet 515, which are all similar to those same elements described with reference to FIG. 4. The magnetic connector 610 additionally includes a cylindrical hub 611, a sliding plunger 612, a second magnet 615 and a magnet enclosure 614. These elements are arranged to form a compression breakaway section and a tensile breakaway section. The compression breakaway section includes the magnet 515 (first magnet) bonded to the sliding plunger 612 and mechanically connected to the actuator-side shaft 517. The compression breakaway section can move (slide) longitudinally inside a cylindrical space 613 (empty space) of the cylindrical hub 611. The tensile breakaway section includes the magnet 615 (second magnet) enclosed in its magnet enclosure 614 which is fixedly bonded to the cylindrical hub 611. Therefore, the compression breakaway magnet 515 can move together with the plunger 612 within the cylinder hub 611, while the tensile breakaway magnet 615 is directly bonded to the cylindrical hub 611.

For the compression breakaway section, in its operational state the magnet 515 creates a magnetically attracting force towards a ferromagnetic wall of the cylindrical hub 611, thereby clamping the plunger 612 against the cylindrical hub 611, at a first plane P1. Altering the thickness T1 of the plunger wall between the magnet 515 and the hub 611 can allow the breakaway force for compressive breakaway to be fine-tuned. For the tensile breakaway section, similarly the magnet 615 is enclosed by the magnetic enclosure 614 which is made of ferromagnetic material so the magnet 615 and its enclosure 614 are fixedly attached to the hub 611, at a second plane P2. The magnet enclosure 614 mates directly against the hub 611, while the magnet 615 is recessed in a pocket created by the enclosure 614. Increasing the depth of this pocket formed by the magnet enclosure 614 (i.e., increasing the air gap T2 between the magnet 615 and the plane P2) allows fine-tuning the breakaway force for tensile breakaway.

In some applications it may be helpful to have different breakaway forces for tension and compression. For example, a smaller compressive breakaway force may be desirable because a kinking failure mode in the drive wire could occur at a lower force than a tensile force. In addition, a kinking failure due to excessive compression force can have more critical consequences on the welfare of the patient if, for example, the catheter tip becomes stuck against the wall of an endoluminal anatomy and the actuator continues compressing (pushing) the drive wire. In contrast, failure due to tensile force (pulling force) has a failure mode of plastic deformation and buckling of the drive wire which usually occurs at a higher force. In particular, when the drive wires are made of pliable material, such as nitinol, which has a high degree of resistance to plastic deformation, the failure due to tensile force can be much higher than compressive force failure.

An advantageous design feature of the embodiment shown in FIG. 6 is that there is no magnetic flux saturation where magnetic fields would enter the vicinity of other actuators or create potentially outside interferences. The inset view B of FIG. 6 shows a graphical representation of the magnetic filed of the first magnet 515. This is achieved by creating a steel loop around the magnet that closes the loop of the magnetic path so that the flux density outside the module is less than 0.1 Tesla. In addition, in at least some embodiments, the first magnet 515 is radially polarized (radial poled) or diametrically poled. A "radially poled" magnet is understood as a magnet system which is poled substantially parallel to the target front face. That is, the magnetic dipoles of this magnet system are substantially situated parallel to the target front face and it is their pole exit (or entry) faces from which the magnetic field perpendicularly exits or enters, respectively, substantially perpendicularly to said target front face. The "radial" components of the magnetic field are understood as components which are parallel to the target front face or, in the case of nonplanar target front faces, parallel to the tangential plane at the target front face, at the front face point closest to the spatial point considered with reference to the magnetic field. According to at least one embodiment, an additional advantage is that the magnetic breakaway (magnetic fuse) would preferably reside on the actuator side, and not on the disposable catheter itself.

FIG. 7A and FIG. 7B graphically illustrate compressive breakaway and tensile breakaway, respectively. As shown in FIG. 7A, compressive breakaway occurs when excessive compression force 710 exists on the mechanical link between catheter-side shaft 512 and the actuator-side shaft 517. In this case, when the compression force 710 exceeds the force created by the magnetic field of first magnet 515 (the compressive force becomes larger than a predetermined compressive value), the sliding-plunger 612 travels a distance D1 inside the cylinder hub 611 in a direction 720 towards the distal end of the steerable instrument 100 (i.e., towards the drive wire). This releases (breaks away) the compressive force between the drive wire 110 and the actuator 310. The travel distance D1 of the sliding plunger 612 relative to the cylinder hub 611 should be larger than the travel of the catheter itself. This is so the plunger 612 does not crash into the other side of the hub 611 potentially causing damage (by backlash).

On the other hand, as shown in FIG. 7B, tensile breakaway occurs when excessive tensile force 730 (pulling force) exists in the mechanical link between actuator-side shaft 517 and the catheter-side shaft 512. In this case, when the tensile force 730 exceeds the force crated by the magnetic field of the second magnet 615 (a predetermined tensile value), the entire cylinder hub 611 becomes decoupled from the catheter-side shaft 512 and steel catch 513. Since the drive wire 110 is experiencing excessive tensile (pulling force), when the magnetic coupling breaks away, the catheter-side shaft 512 travels a distance D2 in a direction 740 away from the cylindrical hub 611 to release the excessive tensile force 730.

When either compressive breakaway or tensile breakaway occurs, the controller of the system uses force feedback to initiate a reattachment routine to prevent over-travel from happening. However, it should be noted that, without additional information, the controller would not be able to tell the difference between tensile or compressive breakaway. Therefore, one solution would be to have the reengage move both forward and backward until the force feedback shows a spike in force. Another solution would be to use physical proximity sensors to read if the plungers are engaged. This could be done with Hall Effect sensors provided at planes P1 and P2 to read the magnetic field from the magnet. A further solution to determine what type of breakaway has occurred would be to set threshold levels for the bending force at which the breakaway occurs. As described above, it is generally more advantageous in terms of patient safety to trigger a breakaway action under compressive force at a threshold level lower than that of a tensile force. These parameters can be preprogrammed (pre-stored) in the memory of the system, so that the controller could compare the force that caused the breakaway with the pre-stored threshold parameters. This could be done by using magnets of different strength for the compression breakaway section and tensile breakaway section.

<FIG. 8-9: Types of Magnetic Connector>

Figure 8B:
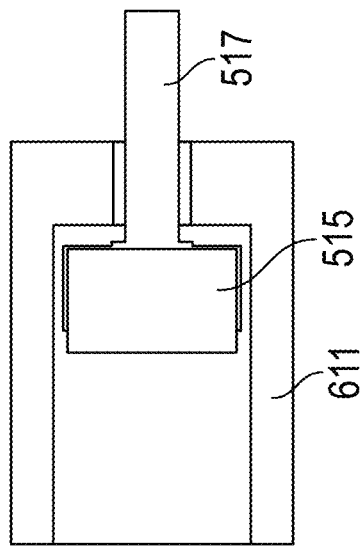
FIG. 8A and FIG. 8B respectively illustrate a perspective view and a cross-sectional view of a first example of a magnetic connector configured as a magnetic fuse.
Figure 8A:
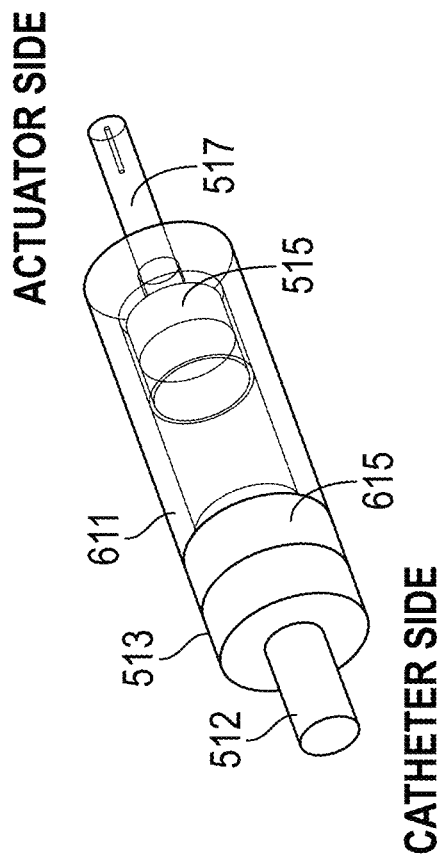

FIG. 8A and FIG. 8B respectively illustrate a perspective view and a cross-sectional vie of a first example of a magnetic connector. According to the first example, the magnetic connector uses a cylindrical magnet 515 which is connected to the actuator-side shaft 517 with adhesives or welding, for example. Therefore, an embodiment of the present disclosure utilizes a plurality of cylindrical magnets 515 for the for the connection hub 500. The use of cylindrical magnets 515 produces the most coupling force per unit area.

Figure 9B:
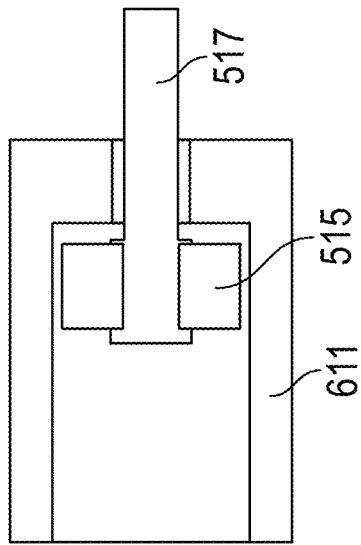
FIG. 9A and FIG. 9B respectively illustrate a perspective view and a cross-sectional view of a second example of a magnetic connector configured as a magnetic fuse.
Figure 9A:
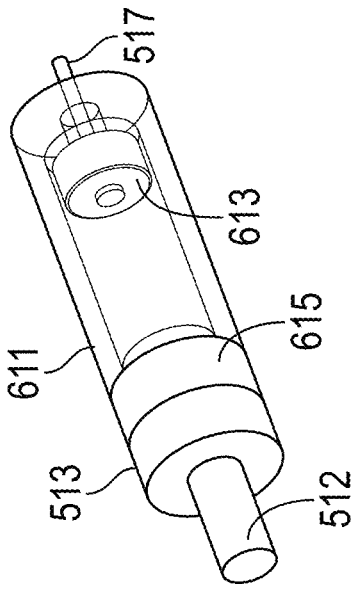

FIG. 9A and FIG. 9B respectively illustrate a perspective view and a cross-sectional view of a second example of a magnetic connector. According to the second example, the magnetic connector uses a ring-shaped magnet 515 which is connected to the actuator-side shaft 517 by mechanical constraints, such as clamping, pressure fitting or bolt fastening. Therefore, a second embodiment of the present disclosure utilizes a plurality of ring-shaped magnets which can allow for mechanical constraint through clamping as opposed to adhesives. Although this design provides a more secure connection between eth magnet and the actuator, it may provide slightly less force per unit area in comparison to first example due to less magnetic material.

<FIG. 10A-10E: Magnetic Connector having Low Force Engagement>

FIG. 10A, FIG. 10B, FIG. 10C, FIG. 10D and FIG. 10E illustrate various views of a magnetic connector hub 500, according to another embodiment of the present disclosure. In the foregoing embodiments, the user performs a single action connection by inserting and twisting the proximal end of the steerable catheter sheath 100 into the magnetic connector hub 500. In the previous embodiment of the magnetic connector hub 500 shown in FIG. 2 and FIG. 3, when the user inserts the catheter sheath 100 into the hub 500 and rotates it in a clockwise direction of arrow 520, the magnetic engagement force can be potentially too strong and could unintentionally transfer movement to the catheter tip. In addition, after engagement, if the user wishes to momentarily disengage the catheter sheath from the magnetic connector hub 500, the users first rotates the sheath in a counter clockwise direction and then the catheter sheath immediately becomes disconnected (removed) from the hub 500. The embodiment shown in FIG. 10A-FIG. 10E provides a magnetic connector hub 500 where partial low force engagement occurs before the twist motion. With this alternate embodiment, an engagement process includes the steps of: (1) home the actuator to initial engagement position, this can be done passively (e.g., manually by the user) or actively by the software system; (2) insert catheter through a guide until slight interference exists between the magnets 515 and drive wires 110, this will automatically align the catheter to the home position. In this position, engagement force is minimal ~<1 N; (3) rotate clockwise to a locked position where catheter is fully engaged (>15 N breakaway); (4) for emergency disengagement, press to unlock and rotate the catheter counterclockwise to disengage fully so the catheter drive wires are free while the catheter hub remains attached to the actuator hub. In other words, according to the embodiment shown in FIG. 10A-FIG. 10E, during the disengagement process, the catheter can remain physically connected and locked to the hub 500 even after the actuator is magnetic decoupled from the drive wires.

Figure 10A:
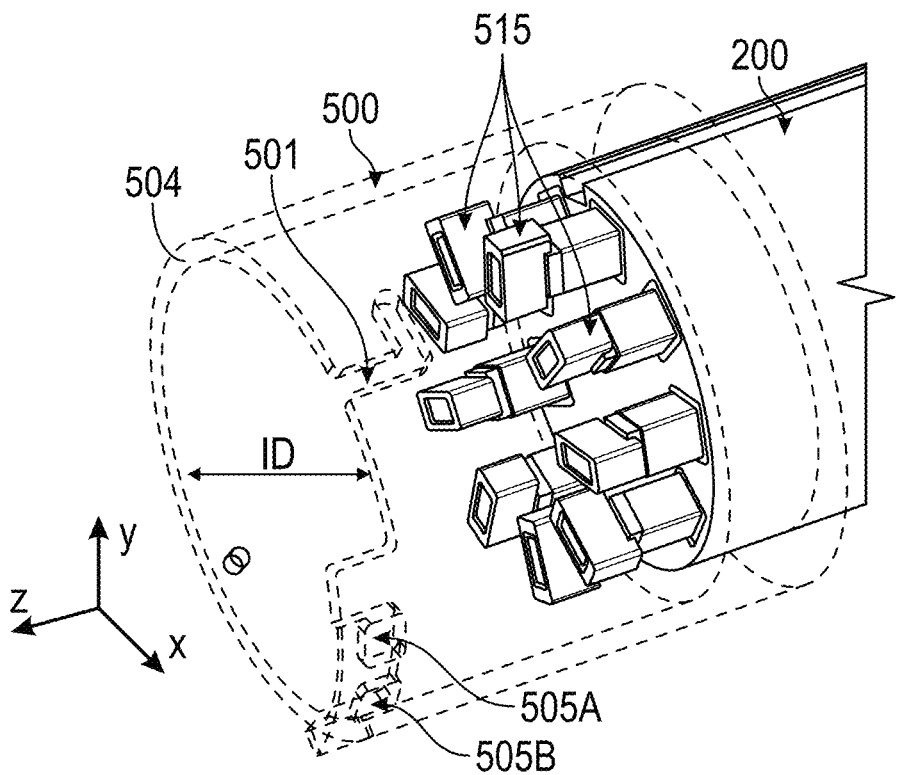

FIG. 10A shows a perspective view of a magnetic connector hub 500 without the steerable instrument 100. FIG. 10B shows a perspective view of the magnetic connector hub 500 connected to the proximal end of the steerable instrument 100 (a steerable catheter sheath) prior to magnetic coupling, according to the present embodiment. As shown in FIG. 10A, in this embodiment, the connector hub 500 includes a cylindrical housing 504 attached to or integrated with the handle 200 on the actuator side of the system 1000. The housing 504 is so dimensioned with an inner diameter (ID) configured to receive therein an outer diameter of the proximal end of the steerable instrument 100. A plurality of magnetic connectors 510 are arranged inside the hub 500 at a predetermined pitch radius around a center axis of the hub, in a manner similar to that shown in FIG. 2 and FIG. 3. Each magnetic connector 510 includes a magnet 510 on the actuator side, and a steel catch 513 on the catheter side, this is similar to an arrangement of several (nine in this case) of the magnetic connector 500 shown in FIG. 4.

In the present embodiment, the proximal end of the steerable instrument 100 includes a guiding pin 102 and a biasing lock 103, both of which are functionally similar to the same components shown in FIG. 2 and FIG. 3. The housing 504 of magnetic connector hub 500 includes a keyway 501 for guiding the pin 102 of steerable instrument 100, and plural openings (505A, 505B) for locking the steerable instrument 100 at predetermined rotational positions with respect to the connector hub 500. Specifically, the housing 504 includes a first opening 505A and a second opening 505B which are configured to engage with a locking hook 506 of a biasing lock 503. As shown in FIG. 10B, to connect the catheter to the actuator, the proximal end of the steerable instrument 100 is linearly inserted in a direction of arrow 519 and subsequently rotated (twisted) in a clockwise direction shown by arrow 520.

FIG. 10C illustrates further details of the attachment process, according to the present embodiment. As shown in FIGS. 10B and 10C, when the steerable instrument 100 is first inserted in the direction of arrow 519 into the connector hub 500, the guiding pin 102 advances along a first part of keyway 501. At the position shown in FIG. 10B, the locking hook 506 of biasing lock 503 does not yet engage with either the first opening 505A or the second opening 505B. In addition, as shown in FIG. 10C, the magnet 515 is not yet completely aligned with a corresponding steel catch 513. At the attachment position shown in FIGS. 10B and 10C, there is only slight interference between the still catcher 513 and the magnet 515. However, at this position of minimum interference, a minimal engagement force about 1 Newton or less (~<1 N) will cause each steal catcher 513 and magnet 515 to automatically align to thereby place the catheter to a home position.

FIG. 10D and FIG. 10E illustrate a process of magnetic decoupling (e.g., for emergency purposes) while the catheter remains physically attached to the connector hub 500. FIG. 10D shows a first locked position where the proximal end of the steerable instrument 100 is fully attached to the connector hub 500, and where the steel catcher 513 and magnet 515 of each magnetic connector 510 are aligned and magnetically coupled. FIG. 10D shows the position after the catheter is rotated clockwise in the direction of arrow 520 to first locked position where the magnetic coupling force in the entire hub is >15 N (i.e., a breakaway force greater than 15 N is required to magnetically decouple all magnets 515 from the corresponding steel catchers 513). In this coupling process, the guiding pin 102 of the catheter 100 follows the keyway 501 of the housing 504 in the clockwise direction, and the biasing lock 503 causes the locking hook 506 to engage with the first opening 505A to lock the steerable instrument 100 in a first locked position (locked position 1) with respect to the housing 504. This first locked position occurs when the catheter is attached to the actuator, and all of the magnets 515 are aligned and magnetically coupled with corresponding steel catchers 513.

In the event that there is a need for decoupling the magnetic connection without physically detaching the catheter from the connector hub 500, the user can press the biasing lock 203 to disengage the locking hook 506 from the first opening 506A, and then rotate the instrument 100 in the counterclockwise direction. In this manner, as shown in FIG. 10E, the guiding pin 502 moves along the keyway 501 in the counterclockwise direction and the locking hook 506 engages with the second opening 505B to place the catheter in a second locked position (locked position 2). In the second locked position, the magnetic coupling of each magnetic connector 510 is decoupled without disengaging the instrument 100 from the connector hub 500. The design of the keyway 501 is an important aspect that allows the possibility of magnetically decoupling the magnetic connector 510 without mechanically disengaging the catheter from the connector hub 500. To that end, as shown in FIG. 10B, FIGS. 10D and 10E, the keyway 501 is a multi-directional keyway configured to place the steerable instrument 100 in a plurality connection states with respect to the connector hub 500. In one embodiment, keyway 501 is a "T" shaped keyway which allows for the guiding pin 502 to move first in a lengthwise direction (along the length of the "T") followed by clockwise and/or counterclockwise movements (along the width of the "T").

Figure 11:
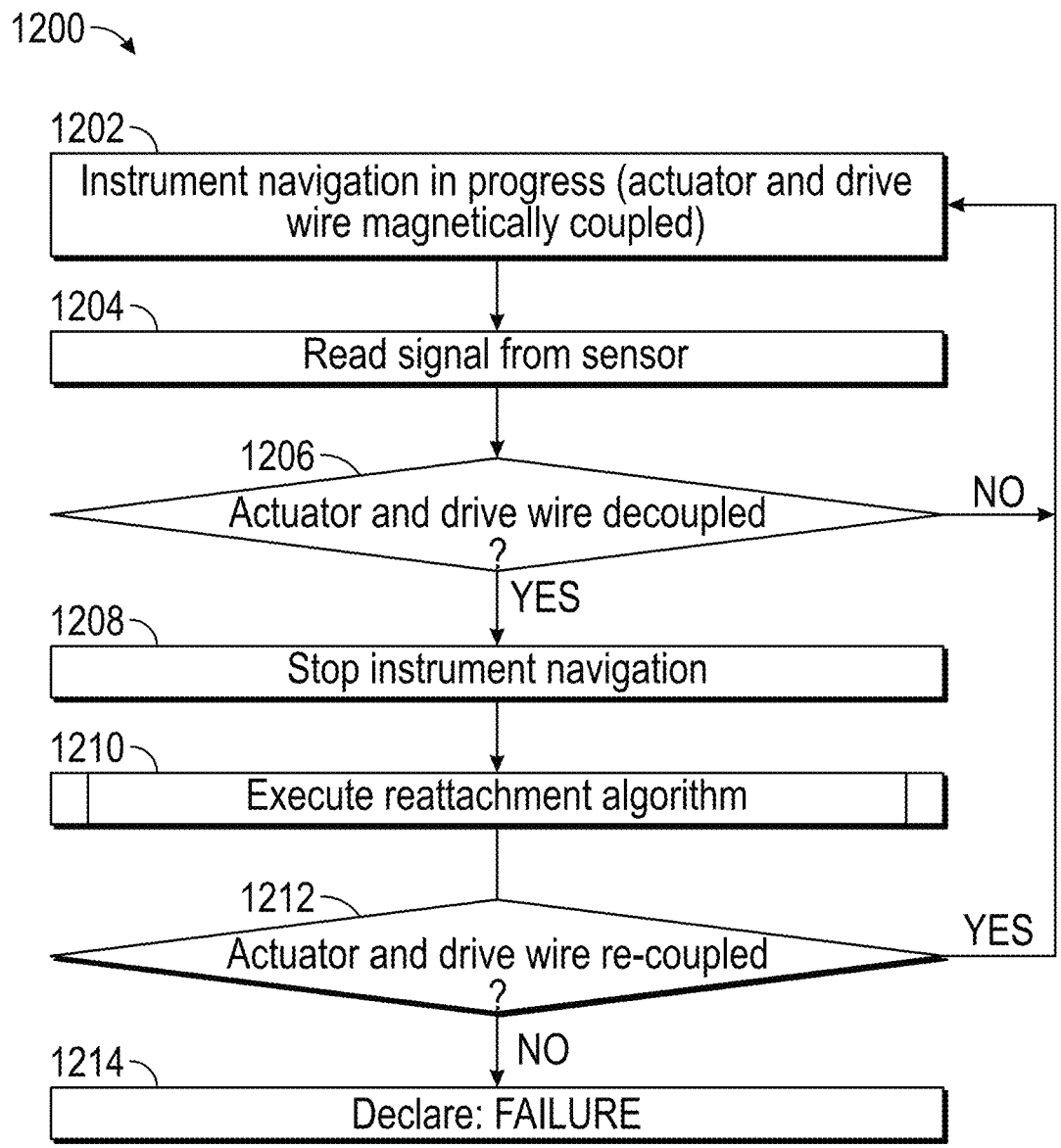
FIG. 11 illustrates an exemplary process for implementing breakaway and recoupling control of the steerable instrument 100 with the actuator system 300 of the continuum robot system 1000, according to the present disclosure.
Figure 12:
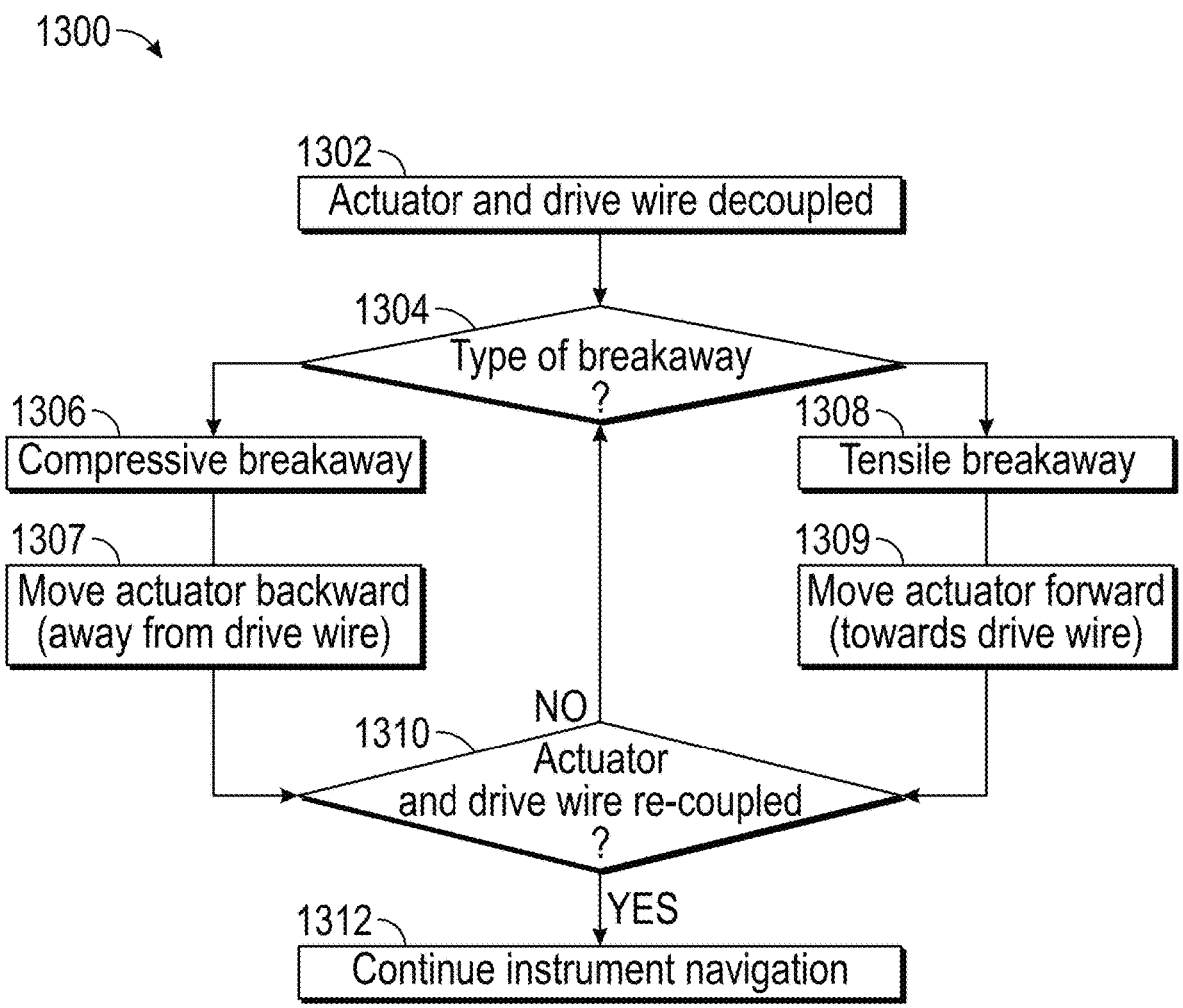
FIG. 12 illustrates an exemplary process for implementing a reattachment algorithm of step 1210, according to the present disclosure.

<FIG. 11-12: Breakaway and Recoupling Control Algorithms>

FIG. 11 illustrates an exemplary process for implementing breakaway and recoupling control of the steerable instrument 100 with the controller of the continuum robot system 1000, according to the present disclosure. According to at least one embodiment, the controller 320 and/or CPU 410 controls the steerable instrument 100 such that, for example, when an excessive actuation force is applied to at least one drive wire, the actuating force is minimized (brought close to zero) to provide maximum flexibility to the steerable instrument, the actuation force for actuating the drive wires 110 is continually monitored regardless of whether the steerable instrument is actuated during insertion or retraction (withdrawal), and the drive wires 110 can freely breakaway and translate to become compliant when excessive compressive or tensile force is applied.

The workflow of FIG. 11 assumes the steerable instrument 100 is in an actively controlled mode in which, at step 1202, the actuator system 300 (see FIG. 1A) controls the instrument navigation already in progress. That is, at step 1202, the system 300 monitors the navigation of the steering instrument 100 either during catheter insertion or extraction (withdrawal) where the actuator 310 and drive wire 110 are magnetically coupled to each other by the magnetic connector (1510 or 1610). At step 1204, the system 300 reads a signal from a sensor; i.e., the system reads a signal from a strain or position sensor 304. In some embodiments, the strain, position, and/or Hall Effect sensor 304 can be provided at the proximal end of the drive wire 110 (e.g., near the one or more magnets of each magnetic connector). In addition, a position and/or orientation sensor (e.g., EM sensors 190) may also be provided at the distal end of the steerable instrument 100. One or more of these sensors (e.g. sensor 304 or sensor 190 in FIG. 1B) can be used to obtain a signal indicative of an actuation force being applied to the steerable instrument 100. At step 1206, the actuator system 300 continuously monitors the signal from sensor 304 to make a determination as to whether or not the actuator 310 and drive wire 110 become decoupled. As illustrated in the embodiment of FIGS. 7A and 7B, the magnetic connector 610 can become decoupled by compressive breakaway or by tensile breakaway.

At step 1206, if at least one drive wire 110 is experiencing an actuation force close to the failure point, the magnetic connector decouples (breaks away) the magnetic link between the actuator and drive wire (YES in step 1206), and the flow proceeds to step 1208. On the other hand, if the actuating force remains within operating thresholds, the actuator and drive wire remain magnetically coupled by the magnetic connector (NO in step 1206), and the loop repeats.

In step 1208, after determining that the actuator and drive wire have been decoupled, the actuator system 300 momentarily stops navigation of the steerable instrument 100. That is, at step 1208, the controller 320 stops applying the actuation force (e.g., by stopping the actuator or motor). Then, at step 1210, the actuator system 300 initiates an algorithm to re-attach the actuator 310 to the drive wire 110. At step 1212, the actuator system 300 determines if the actuator 310 and the drive wire 110 have been reattached to each other. If the actuator and drive wire have been successfully reattached to each other (YES at 1212), the flow returns to step 1202 to continue instrument navigation. However, if the actuator and drive wire are not reattached to each other (NO at 1212), the actuator system 300 may determine there is a failure and can issue a warning to the user at step 1214.

At step 1206, decoupling is detected based on the status of one or more of the magnetic connectors. If at least one magnetic connector is decoupled (YES in step 1212), e.g., due to bending force being near the failure point, the actuator system 300 stops instrument navigation (at step 1208) to prevent possible damage to the instrument and/or the patient.

FIG. 12 illustrates an exemplary process for implementing a reattachment algorithm of step 1210. The process of FIG. 12 starts at step 1302 when the actuator 310 and drive wire 100 are decoupled by the magnetic connector. At step 1304, the actuator system 300 takes into account the type of breakaway. That is, at step 1304, the actuator system 300 may refer to information stored in the system's memory immediately before the decoupling of breakaway event of step 1206. As explained elsewhere in this disclosure, system can determine if the breakaway occurred due to excessive compressive force (FIG. 7A) or due to excessive tensile force (FIG. 7B). Therefore, in the case that the type of breakaway is compressive breakaway, the flow proceeds to step 1306, and the controller 320 moves the actuator 310 backward in a direction away from the drive wire 110 (step 1307). Specifically, as shown in FIG. 7A, since excessive compressive force 710 causes the magnet 515 and plunger 612 to move inside the cylindrical hub 611, to reattach the actuator to the drive wire, the actuator must pull the actuator-side shaft 517 in a direction opposite to arrow 710. In the case that the type of breakaway is tensile breakaway, the flow proceeds to step 1308, and the controller 320 causes the actuator 310 to move forward in a direction towards the drive wire 110 (step 1309). Specifically, as shown in FIG. 7B, since excessive tensile force 730 causes the magnet 615 and the cylindrical hub 611 to become detached from the catheter-side shaft 512, to reattach the actuator to the drive wire, the actuator must push the actuator-side shaft 517 and the entire cylindrical hub 611 in a direction opposite to arrow 730.

Continuing to refer to FIG. 12, it would be advantageous to perform the reattachment process in an incremental manner to avoid driving the actuator 310 excessively fast or excessively far against the drive wire for reattachment. Therefore, at step 1310, the actuator system 300 continuously and incrementally repeats the reattachment loop until the system determines that the actuator 310 and the drive wire no have been magnetically recoupled. Once magnetic recoupling is confirmed, the flow advances to step 1312 which allows the system to continue instrument navigation.

As noted above, in certain embodiments, the actuator system 300 may not be configured to determine the type of breakaway. In the case that the actuator system 300 determines that the actuator and the drive wire have become decoupled, but the system does not know the type of breakaway, the controller 320 can perform the reattachment process of FIG. 12 incrementally by moving the actuator first in one direction and then in the other (opposite) direction, until the force feedback shows a spike in force. Once the spike in force is detected, the controller can continue driving the actuator according to the direction in which the spike in force was detected. As noted elsewhere in this disclosure, reattachment or recoupling of the actuator 310 to the drive wire 110 can be monitored based on force feedback control provided by one or more sensors 304 and feedback signal 305. Another solution is to use physical proximity sensors to read if the plungers of the magnetic connector are reengaged. This could be done with Hall Effect sensors that read the magnetic field from the magnet(s).

The foregoing disclosure provides at least the following advantageous features.

The connection is magnetic and does not require manual latching. It also has the ability to attach a multiplicity of modules in a single user motion. The design is also unique as it creates a breakaway feature. This is an important feature as it prevents damage to the catheter/tool and/or patient when it experiences an excessive force. This adds a safety element and helps protect the patient. And when the breakaway occurs the catheter can be easily reengaged without damage and normal operation can resume. Connection can also be broken at any point in the operation.

Another advantage of this disclosure is that multiple individual connections are made concurrently unlike prior art documents. The relevant prior art does not include a feature that allows multiple connections to be made in a simple motion. Another advantage of this disclosure is that the connection is not static, but dynamic allowing for axial motion along the connecting modules. Also a failure in connection in the relevant art results in leaks, while this disclosure allows for automatic resumption of operation.

Furthermore, connection between catheter and actuator is created magnetically. No additional action, such as latching, is required to create the connection. The connection is made between multiple independent actuators with a single motion. This can be completed through an insert and twist motion by the user. An engagement routine is then operated by the controller to complete magnetic coupling. Breakaway occurs under significant force allowing as a safety mechanism. Connection can be broken at any position in actuator travel. This allows for disconnection in power down situations.

This present disclosure has an additional advantage over the relevant art as it allows for compressive and tensile breakaway and subsequent re-attachment thereof. Since conventional magnetic breakaway allows for tensile breakaway only, the capacity to provide tensile and compressive breakaway is very advantageous from a safety perspective, as it can prevent kinking and herniation of the drive wire which could otherwise cause harm to the patient.

The magnetic connector described in the present disclosure also couples the actuator directly to the actuating mechanism (the tendon or drive wire) and not the body of the steerable instrument. In this manner, the magnetic connector protects the tendon or drive wire from failure. Conventional magnetic breakaway techniques purport to protect the body of the instrument from failure, but do not protect the actuating mechanism such as the drive wire or tendon itself. If conventional breakaway techniques were applied to a robotically steerable catheter such techniques would not prevent kinking as it would only create breakaway between the catheter body and the actuator, but would not provide breakaway between the manipulating drive wire and the actuator.

Figure 13:
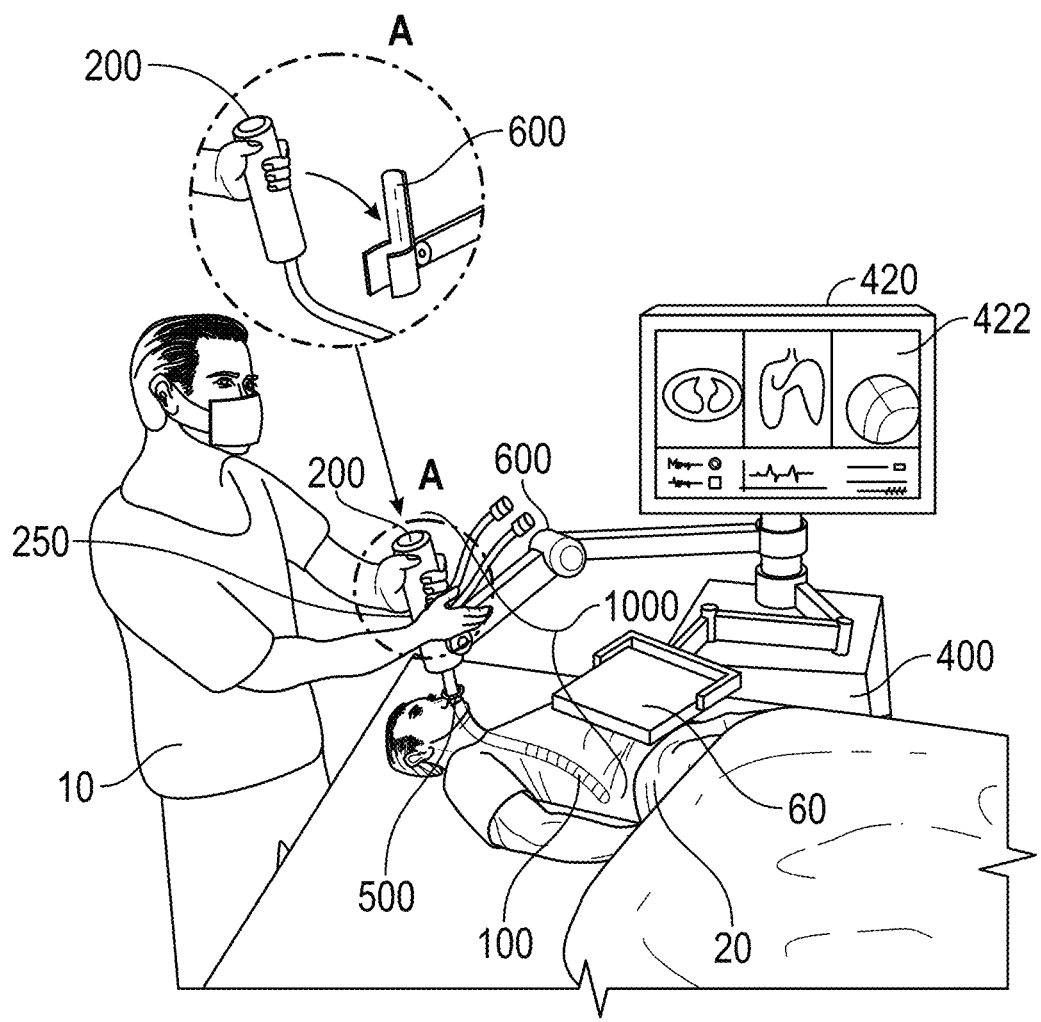
FIG. 13 illustrates an example use-case scenario of the system 1000 for a medical procedure of a patient.

<FIG. 13: Exemplary Use-Case Scenario>

According to a use-case scenario of the robotic medical system 1000, as illustrated in FIG. 13, during a procedure for a patient 20, the screen 422 of display 420 may prompt a user 10 (e.g., a physician) to connect a new catheter 100 to the robotic platform 600. In this case, for safety reasons, the user 10 may first demagnetize the magnetic connection hub 500 with an electrical signal via direct current (DC) voltage from the computer or console 400. Then, the user connects the new catheter 100 to handle 200 via the magnetic connection hub 500 with a single "slide and twist" motion. The connection may include a sliding motion in a linear direction substantially parallel to the length-wise direction of the catheter, and a twist motion (rotation) in either clockwise (CW) or counter clockwise (CCW) direction. Alternatively, the connection may include only a linear motion (sliding motion) in which the proximal end of the catheter is linearly moved along a mechanical guide such as a ridge or groove to ensure coaxial alignment between the actuator unit (motor) and the drive wires of the new catheter. In the case of only linear engagement of catheter to magnetic connection hub 500, the same locking mechanism shown in FIG. 2 can be used to lock in place the catheter.

Upon connection of the new catheter 100, the system 1000 may prompt the user 10 to confirm the catheter connection via the screen 422, a keyboard, or other system user interface (UI). Once connection of the new catheter is confirmed by the user, the magnetic mechanism of the connection hub 500 is magnetized via DC voltage, and the motor (actuator) and drive wire can move in unison to control the bending and navigation operations of the catheter. When the procedure is complete, the user can tell the system that the procedure is complete via the screen, the keyboard, or other UI. The system 1000 stops the operations of the catheter 100, and before the catheter 100 is removed, system 1000 demagnetizes the magnetic connection hub 500 via DC voltage. Then the system screen 422 can inform the user that removal of the catheter from the connection hub 500 is safe to complete. Here, it should be noted that voltage controlled activation and deactivation of the magnetic connection hub 500 can be implemented as a safety procedure to avoid magnetic interaction of the connection hub with surrounding medical devices and/or metallic instruments. However, the mechanical actuation of each individual drive wire magnetically coupled to a corresponding actuator via a magnetic fuse 510 is done without the need of any voltage.

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

According to the various embodiments disclosed herein, a robotically steerable medical apparatus comprises an elongate body (100) having a tubular opening (105) and a plurality of channels (104) arranged along a wall of the elongate body substantially surrounding to the tubular opening (105), the elongate body having a steerable section (103) and a non-steerable section (102); a drive wire (110) is arranged in each channel (104) and configured to manipulate the steerable section (103) of the elongate body (100); an actuator unit (310) is configured to apply an actuation force to the drive wire (110) arranged in each channel (104); a magnetic connector (510) is configured to magnetically couple the actuator unit (310) to the drive wire (110) via at least one magnet; and a controller (320) is configured to determine a connection status of the magnetic connector (510) and control the actuator unit (310) according to the connection status of the magnetic connector.

The magnetic connector 510 servers as a magnetic fuse comprising a pair of magnetically coupled shafts. The magnetic fuse comprises a cylindrical hub 611 with two plungers respectively attached to the shafts, one on each side of the cylindrical hub, and two magnetic breakaway points. The two breakaway points of the magnetic fuse provide has a bi-directional breakaway force. The magnetic fuse allows breakaway to occur under a compressive force applied to the two shafts, which could prevent wire kinking and herniation. The magnetic fuse allows breakaway to occur under a tensile force applied to the two shafts, which could prevent plastic deformation and/or fracture of drive wires. The magnetic fuse is configured to return to normal operation after recoupling. The magnetic fuse utilizes force feedback or other similar technique to sense disengagement and initialize reengagement routine.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A robotically steerable medical apparatus, comprising:
an elongate body having a tubular opening and a plurality of channels arranged along a wall of the elongate body substantially surrounding to the tubular opening, the elongate body having a steerable section and a non-steerable section;
a drive wire arranged in a channel and configured to manipulate the steerable section of the elongate body;
an actuator unit configured to apply an actuation force to the drive wire;
a magnetic connector configured to magnetically couple the actuator unit to the drive wire; and
a controller configured to determine a coupling state of the magnetic connector and control the actuator unit according to the coupling state of the magnetic connector,
wherein, in a first coupling state of the magnetic connector where the actuator unit is magnetically coupled to the drive wire, the controller causes the actuator unit to move in a first translational motion to transmit the actuation force along the drive wire to manipulate the steerable section of the elongate body, and
wherein, in a second coupling state of the magnetic connector where the actuator unit is magnetically decoupled from the drive wire, the controller causes the actuator unit to move in a second translational motion to magnetically recouple the actuator unit to the drive wire.

2. The apparatus according to claim 1,
wherein the magnetic connector comprises a catheter-side shaft and an actuator-side shaft magnetically coupled to each other via at least one magnet,
wherein the at least one magnet is provided in the actuator-side shaft and/or in the catheter-side shaft, and
wherein the catheter-side shaft is mechanically attached to the drive wire and the actuator-side shaft is mechanically attached to the actuator unit.

3. The apparatus according to claim 2, further comprising:
a sensor configured to detect the actuation force applied to the drive wire,
wherein, based on a predetermined value of the actuation force detected by the sensor, the controller determines the coupling state of the magnetic connector.

4. The apparatus according to claim 2,
wherein the catheter-side shaft and/or the actuator-side shaft are/is configured to decouple from the at least one magnet at a predetermined value of the actuating force applied to the drive wire.

5. The apparatus according to claim 3,
wherein the actuating force includes one or more of a tensile force, a compressive force, and a torque.

6. The apparatus according to claim 5,
wherein, when the actuating force applied by the actuator unit to the drive wire is a tensile force larger than a predetermined tensile value, the magnetic connector changes from the first coupling state to the second coupling state due to tensile breakaway, and
wherein the controller causes the actuator unit to move the actuator-side shaft in a linear direction towards the drive wire to magnetically recouple the actuator unit to the drive wire.

7. The apparatus according to claim 5,
wherein, when the actuating force applied by the actuator unit to the drive wire is a compressive force larger than the predetermined value, the magnetic connector changes from the first coupling state to the second coupling state due to compressive breakaway, and
wherein the controller causes the actuator unit to move the actuator-side shaft in a linear direction away from the drive wire to magnetically recouple the actuator unit to the drive wire.

8. The apparatus according to claim 5,
wherein, when the actuating force applied by the actuator unit to the drive wire is a torque larger than a predetermined value, the magnetic connector changes from the first coupling state to the second coupling state due to lateral or rotational breakaway.

9. The apparatus according to claim 2,
wherein the magnetic connector includes a first magnet and a second magnet enclosed in a cylindrical hub, and
wherein, in the first coupling state of the magnetic connector where the actuator unit is magnetically coupled to the drive wire, the second magnet is magnetically coupled to the catheter-side shaft and the first magnet is mechanically attached to the actuator-side shaft and magnetically coupled to the cylindrical hub.

10. The apparatus according to claim 9,
wherein, when the actuating force applied by the actuator unit to the drive wire is a tensile force larger than a predetermined tensile value, the magnetic connector changes from the first coupling state to the second coupling state due to tensile breakaway, and
wherein, in the second coupling state of the magnetic connector where the actuator unit is magnetically decoupled from the drive wire, the controller causes the actuator unit to move one or more of the first and second magnets in a direction opposite to the tensile force to magnetically recouple the actuator unit to the drive wire.

11. The apparatus according to claim 9,
wherein, when the actuating force applied by the actuator unit to the drive wire is a tensile force larger than a predetermined tensile value, the magnetic connector changes from the first coupling state to the second coupling state due to tensile breakaway,
wherein, upon tensile breakaway, the drive wire moves in a linear direction opposite to a direction of the tensile force, and
wherein, upon the tensile breakaway, the controller causes the actuator unit to move both the first magnet and the second magnet in a linear direction towards the drive wire to magnetically recouple the actuator unit to the drive wire.

12. The apparatus according to claim 9,
wherein, when the actuating force applied by the actuator unit to the drive wire is a compressive force larger than a predetermined compressive value, the magnetic connector changes from the first coupling state to the second coupling state due to compressive breakaway,
wherein, upon compressive breakaway, the first magnet moves inside the cylindrical hub in a direction towards the drive wire without pushing the drive wire, and
wherein, in the second coupling state of the magnetic connector where the actuator unit is magnetically decoupled from the drive wire, the controller causes the actuator unit to move only the first magnet in a linear direction opposite to the compressive force to magnetically recouple the actuator unit to the drive wire.

13. The apparatus according to claim 9,
wherein the first magnet is a radial poled rare-earth magnet configured to magnetically couple to the cylindrical hub, and the second magnet is an axially poled rare-earth magnet configured to magnetically couple with the catheter-side shaft.

14. The apparatus according to claim 2,
wherein the at least one magnet includes a single permanent magnet provided in the actuator-side shaft,
wherein the single permanent magnet is a cylindrical-shaped magnet or a disc-shaped magnet fixedly attached to the actuator-side shaft, and
wherein the single permanent magnet is an axially poled magnet.

15. The apparatus according to claim 1, further comprising:
a plurality of magnetic connectors including the magnetic connector;
a plurality of drive wires including the drive wire;
a plurality of actuator units including the actuator unit, and
a connector hub having a housing configured to at least partially enclose therein the plurality of magnetic connectors and the plurality of actuator units,
wherein the plurality of magnetic connectors is configured to magnetically couple the plurality of actuator units with the plurality of the drive wires.

16. The apparatus according to claim 15,
wherein the housing of the connector hub is a cylindrical housing which includes a multi-direction keyway and one or more locking positions,
wherein, in the first coupling state of the magnetic connector, the housing locks the elongate body with respect to the connector hub at a first locked position such that the plurality of actuator units are aligned with and magnetically coupled to the plurality of drive wires, and
wherein, in the second coupling state of the magnetic connector, the housing locks the elongate body with respect to the connector hub at a second locked position such that the plurality of actuator units are magnetically decoupled from the plurality of drive wires while the elongate body remains mechanically connected to the connector hub.

17. The apparatus according to claim 15,
wherein the multi-direction keyway of the cylindrical housing is configured to enable mechanical connection of the elongate body to the connector hub in a plurality of connecting states,
wherein, in a first connecting state, the elongate body is guided by the multi-direction keyway into the connector hub in a linear direction such that a minimum interference exists between the plurality of actuator units and the plurality of driving wires,
wherein, in a second connecting state, the elongate body is guided by the multi-direction keyway in a first rotational direction with respect to the connector hub such that the plurality of actuator units and the plurality of driving wires become magnetically coupled to each other by the plurality of magnetic connectors, and
wherein, in a third connecting state, the elongate body is guided by the multi-direction keyway in a second rotational direction opposite to the first rotational direction with respect to the connector hub such that the plurality of actuator units and the plurality of driving wires become magnetically decoupled from each other, while the elongate body remains mechanically connected to the connector hub.

18. A system, comprising:
an elongate body having a tubular opening substantially concentric with a longitudinal axis thereof and extending from a proximal end to a distal end, the elongate body including a non-steerable section and one or more steerable sections located in this order from the proximal end to the distal end;
a plurality of drive wires arranged in a lengthwise direction along a wall of the elongate body so as substantially surround the tubular opening, each drive wire having a distal end thereof attached to one the one or more steerable sections of the elongate body;
an actuator unit configured to apply an actuating force to a drive wire to steer at least one of the one or more steerable sections of the elongate body;
a connector hub configured to mechanically connect the proximal end of the elongate body to the actuator unit;
a magnetic connector arranged in the connector hub and configured to magnetically couple the actuator unit to a proximal end of the drive wire, and
a controller configured to place the actuator unit and the drive wire in a magnetically coupled position or in a magnetically decoupled position via the magnetic connector,
wherein the controller is configured to, based on a predetermined value of the actuating force applied by the actuator unit to the drive wire, change the actuator unit from the magnetically coupled position to the magnetically decoupled position or vice versa, and
wherein the connector hub is configured to maintain the proximal end of the elongate body mechanically connected to the actuator unit regardless of a change from the magnetically coupled position to the magnetically decoupled position or vice versa.

19. The system according to claim 18,
wherein the actuator unit includes a plurality of actuators, and
wherein, during a connection process of attaching the elongate body to the actuator unit, a user inserts the proximal end of the elongate body into the actuator unit in a linear direction and rotates the elongate body in a first rotational direction to simultaneously align the plurality of actuators to the plurality of the drive wires in a one-to-one correspondence.

20. The system according to claim 19,
wherein the magnetic connector includes a plurality of magnets, such that one or more magnets are arranged to magnetically couple each drive wire to each actuator,
wherein the controller is configured to determine that the user has completed the connection process of attaching the elongate body to the actuator unit, and
wherein, upon determining completion of the connection process, the controller performs an engagement procedure where the actuator moves the plurality of actuators towards the plurality of drive wires, such that magnetic coupling occurs between the plurality of actuators and the plurality of drive wires via the plurality of magnets.

21. The system according to claim 19,
wherein the actuating force applied by the actuator unit to the drive wire includes one or more of a tensile force, a compressive force, and a torque.

22. The system according to claim 21,
wherein, when the actuating force applied by the actuator unit to the drive wire includes a tensile force larger than the predetermined tensile value, the actuator unit changes from the magnetically coupled position to the magnetically decoupled position due to tensile breakaway, and
wherein, upon tensile breakaway, the controller causes the actuator unit to move at least one actuator in a linear direction towards the distal end of the elongate body to change from the decoupled position to the coupled position.

23. The system according to claim 21,
wherein, when the actuating force applied by the actuator unit to the drive wire includes a compressive force larger than a predetermined compressive value, the actuator unit changes from the magnetically coupled position to the magnetically decoupled position due to compressive breakaway, and
wherein, upon compressive breakaway, the controller controls the actuator unit to move at least one actuator in a linear direction opposite to a direction of the compressive force to change from the magnetically decoupled position to the magnetically coupled position.

* * * * *